(12) United States Patent
Greenan et al.

(10) Patent No.: US 8,473,030 B2
(45) Date of Patent: Jun. 25, 2013

(54) VESSEL POSITION AND CONFIGURATION IMAGING APPARATUS AND METHODS

(75) Inventors: Trevor Greenan, Santa Rosa, CA (US); Dwayne Yamasaki, Rohnert Park, CA (US); Walter Bruszewski, Guerneville, CA (US); Ken Gardeski, Plymouth, MN (US); David Simon, Boulder, CO (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1382 days.

(21) Appl. No.: 11/622,935

(22) Filed: Jan. 12, 2007

(65) Prior Publication Data
US 2008/0171934 A1    Jul. 17, 2008

(51) Int. Cl.
*A61B 5/055* (2006.01)
(52) U.S. Cl.
USPC .......................................... 600/423; 600/422
(58) Field of Classification Search
USPC ................ 600/407, 410, 414, 415, 423, 424, 600/426, 433, 437, 462, 464, 466, 467; 623/1.11, 1.13, 1.15, 1.23, 1.34
See application file for complete search history.

(56) References Cited

U.S. PATENT DOCUMENTS

| | | | |
|---|---|---|---|
| 5,067,491 A | 11/1991 | Taylor, II et al. | |
| 5,174,295 A | 12/1992 | Christian et al. | |
| 5,273,025 A * | 12/1993 | Sakiyama et al. | 600/145 |
| 5,380,270 A | 1/1995 | Ahmadzadeh | |
| 5,380,320 A | 1/1995 | Morris | |
| 5,383,454 A | 1/1995 | Bucholz | |
| 5,471,982 A | 12/1995 | Edwards et al. | |
| 5,562,728 A * | 10/1996 | Lazarus et al. | 623/1.14 |
| 5,592,939 A | 1/1997 | Martinelli | |
| 5,617,878 A | 4/1997 | Taheri | |
| 5,665,103 A | 9/1997 | LaFontaine et al. | |
| 5,669,905 A | 9/1997 | Scheldrup et al. | |
| 5,701,901 A * | 12/1997 | Lum et al. | 600/463 |
| 5,851,183 A | 12/1998 | Bucholz | |
| 5,871,445 A | 2/1999 | Bucholz | |
| 5,891,128 A | 4/1999 | Gia et al. | |

(Continued)

FOREIGN PATENT DOCUMENTS

| EP | 1391181 | 2/2004 |
|---|---|---|
| EP | 1519140 | 3/2005 |

(Continued)

OTHER PUBLICATIONS

U.S. Appl. No. 11/276,512, filed Mar. 3, 2006, Marilla.

(Continued)

*Primary Examiner* — Tse Chen
*Assistant Examiner* — Rochelle Reardon

(57) ABSTRACT

One or more markers or sensors are positioned in the vasculature of a patient to facilitate determining the location, configuration, and/or orientation of a vessel or certain aspects thereof (e.g., a branch vessel), determining the location, configuration and/or orientation of a endovascular devices prior to and during prosthesis deployment as well as the relative position of portions of the vasculature and devices, generating an image of a virtual model of a portion of one or more vessels (e.g., branch vessels) or devices, and/or formation of one or more openings in a tubular prosthesis in situ to allow branch vessel perfusion when the prosthesis is placed over one or more branch vessels in a patient (e.g., when an aortic abdominal artery stent-graft is fixed to the aorta superior to the renal artery ostia).

13 Claims, 17 Drawing Sheets

U.S. PATENT DOCUMENTS

| | | | |
|---|---|---|---|
| 5,913,820 A | 6/1999 | Bladen et al. | |
| 5,983,126 A | 11/1999 | Wittkampf | |
| 6,086,532 A | 7/2000 | Panescu et al. | |
| 6,104,944 A | 8/2000 | Martinelli | |
| 6,123,714 A | 9/2000 | Gia et al. | |
| 6,235,038 B1 | 5/2001 | Hunter et al. | |
| 6,258,098 B1 | 7/2001 | Taylor et al. | |
| 6,264,662 B1 | 7/2001 | Lauterjung | |
| 6,266,552 B1 | 7/2001 | Slettenmark | |
| 6,280,385 B1 | 8/2001 | Melzer et al. | |
| 6,332,089 B1 * | 12/2001 | Acker et al. | 600/424 |
| 6,363,940 B1 | 4/2002 | Krag | |
| 6,425,914 B1 | 7/2002 | Wallace et al. | |
| 6,470,207 B1 | 10/2002 | Simon et al. | |
| 6,474,341 B1 | 11/2002 | Hunter et al. | |
| 6,493,573 B1 | 12/2002 | Martinelli et al. | |
| 6,522,907 B1 | 2/2003 | Bladen et al. | |
| 6,575,168 B2 | 6/2003 | LaFontaine et al. | |
| 6,579,311 B1 | 6/2003 | Makower | |
| 6,589,230 B2 | 7/2003 | Gia et al. | |
| 6,592,939 B1 | 7/2003 | Yu | |
| 6,623,493 B2 | 9/2003 | Wallace et al. | |
| 6,676,694 B1 | 1/2004 | Weiss | |
| 6,757,557 B1 | 6/2004 | Bladen et al. | |
| 6,812,842 B2 | 11/2004 | Dimmer | |
| 6,822,570 B2 | 11/2004 | Dimmer et al. | |
| 6,833,814 B2 | 12/2004 | Gilboa et al. | |
| 6,838,990 B2 | 1/2005 | Dimmer | |
| 6,889,833 B2 | 5/2005 | Seiler et al. | |
| 6,940,941 B2 | 9/2005 | Gregerson et al. | |
| 6,960,217 B2 | 11/2005 | Bolduc | |
| 6,977,504 B2 | 12/2005 | Wright et al. | |
| 7,001,045 B2 | 2/2006 | Gregerson et al. | |
| 7,026,927 B2 | 4/2006 | Wright et al. | |
| 7,135,978 B2 | 11/2006 | Gisselberg et al. | |
| 7,174,201 B2 | 2/2007 | Govari et al. | |
| 7,566,308 B2 | 7/2009 | Stahmann | |
| 7,676,268 B2 | 3/2010 | Hettrick et al. | |
| 2001/0003985 A1 | 6/2001 | La Fontaine et al. | |
| 2002/0087186 A1 | 7/2002 | Shelso | |
| 2002/0169377 A1 * | 11/2002 | Khairkhahan et al. | 600/433 |
| 2002/0183628 A1 | 12/2002 | Reich et al. | |
| 2002/0193685 A1 | 12/2002 | Mate et al. | |
| 2003/0052785 A1 | 3/2003 | Gisselberg et al. | |
| 2003/0073901 A1 | 4/2003 | Simon et al. | |
| 2003/0117135 A1 | 6/2003 | Martinelli et al. | |
| 2003/0130689 A1 | 7/2003 | Wallace et al. | |
| 2004/0013225 A1 | 1/2004 | Gregerson et al. | |
| 2004/0013239 A1 | 1/2004 | Gregerson et al. | |
| 2004/0093063 A1 | 5/2004 | Wright et al. | |
| 2004/0097805 A1 | 5/2004 | Verard et al. | |
| 2004/0097806 A1 | 5/2004 | Hunter et al. | |
| 2004/0097965 A1 | 5/2004 | Gardeski et al. | |
| 2004/0170254 A1 | 9/2004 | Gregerson et al. | |
| 2004/0179643 A1 | 9/2004 | Gregerson et al. | |
| 2004/0215071 A1 | 10/2004 | Frank et al. | |
| 2005/0038337 A1 | 2/2005 | Edwards | |
| 2005/0085715 A1 | 4/2005 | Dukesherer et al. | |
| 2005/0085720 A1 | 4/2005 | Jascob et al. | |
| 2005/0090843 A1 | 4/2005 | Bolduc | |
| 2005/0099290 A1 | 5/2005 | Govari | |
| 2005/0113906 A9 | 5/2005 | Bolduc et al. | |
| 2005/0172471 A1 | 8/2005 | Vietmeier | |
| 2005/0222668 A1 | 10/2005 | Schaeffer et al. | |
| 2006/0025677 A1 | 2/2006 | Verard et al. | |
| 2006/0094923 A1 | 5/2006 | Mate | |
| 2006/0095119 A1 | 5/2006 | Bolduc | |
| 2006/0149350 A1 | 7/2006 | Patel et al. | |
| 2006/0265049 A1 | 11/2006 | Gray et al. | |
| 2006/0285738 A1 * | 12/2006 | Boese et al. | 382/131 |
| 2007/0023424 A1 | 2/2007 | Weber | |
| 2007/0055359 A1 | 3/2007 | Messer et al. | |
| 2007/0057794 A1 | 3/2007 | Gisselberg et al. | |
| 2007/0135803 A1 | 6/2007 | Belson | |
| 2007/0164900 A1 | 7/2007 | Schneider et al. | |
| 2007/0208252 A1 | 9/2007 | Makower | |
| 2007/0208256 A1 | 9/2007 | Marilla | |
| 2007/0238984 A1 * | 10/2007 | Maschke et al. | 600/424 |
| 2008/0065141 A1 | 3/2008 | Holman | |
| 2008/0208317 A1 | 8/2008 | Jang et al. | |
| 2008/0269596 A1 | 10/2008 | Revie et al. | |

FOREIGN PATENT DOCUMENTS

| | | |
|---|---|---|
| WO | WO96/11624 | 4/1996 |
| WO | WO98/38939 | 9/1998 |
| WO | WO99/59479 | 11/1999 |
| WO | WO01/34061 | 5/2001 |
| WO | WO02/100485 | 12/2002 |
| WO | WO2004/105637 | 12/2004 |
| WO | WO2005/037076 | 4/2005 |
| WO | WO2006/031765 | 3/2006 |
| WO | WO2007/055654 | 5/2007 |

OTHER PUBLICATIONS

U.S. Appl. No. 11/557,204, filed Nov. 7, 2006, Bruszewski et al.

Haga et al., "Small Diameter Active Catheter Using Shape memory Alloy" Proceedings of the 11th Annual Workshop on MEMS, IEEE Jan. 25-29, 1998 pp. 419-424.

* cited by examiner

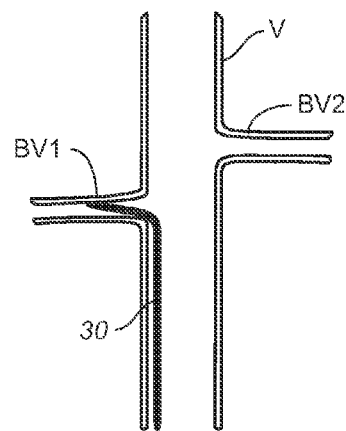
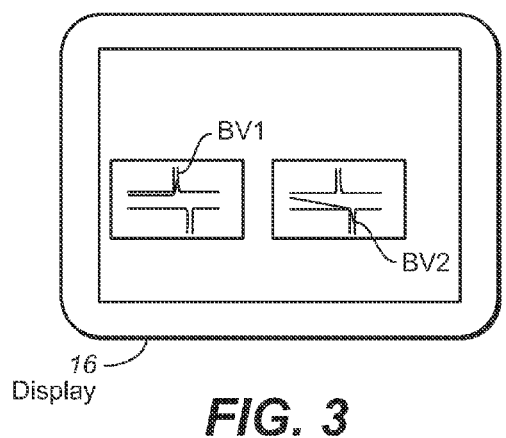
FIG. 2                    FIG. 3
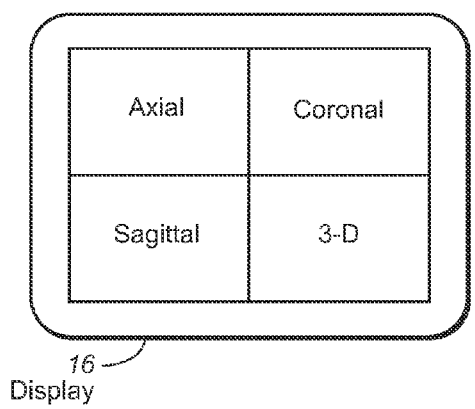
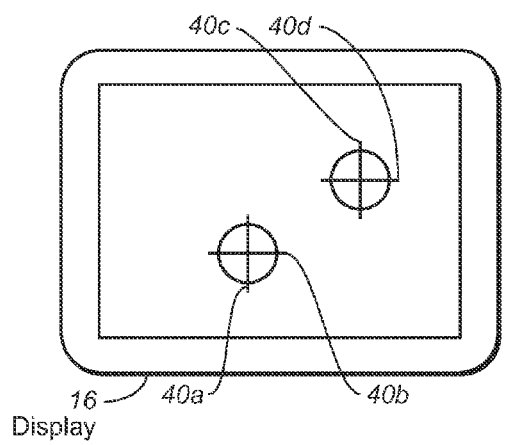
FIG. 4                    FIG. 5

VESSEL POSITION AND CONFIGURATION IMAGING APPARATUS AND METHODS

FIELD OF THE INVENTION

The invention relates to prosthesis deployment and more particularly to locating a branch passageway in a human body such as a branch artery prior to prosthesis deployment or locating a passageway in a prosthesis prior to in-vivo cannulation thereof.

BACKGROUND OF THE INVENTION

Tubular prostheses such as stents, grafts, and stent-grafts (e.g., stents having an inner and/or outer covering comprising graft material and which may be referred to as covered stents) have been widely used in treating abnormalities in passageways in the human body. In vascular applications, these devices often are used to replace or bypass occluded, diseased or damaged blood vessels such as stenotic or aneurysmal vessels. For example, it is well known to use stent-grafts, which comprise biocompatible graft material (e.g., Dacron® or expanded polytetrafluoroethylene (ePTFE)) supported by a framework (e.g., one or more stent or stent-like structures), to treat or isolate aneurysms. The framework provides mechanical support and the graft material or liner provides a blood barrier.

Aneurysms generally involve abnormal widening of a duct or canal such as a blood vessel and generally appear in the form of a sac formed by the abnormal dilation of the duct or vessel wall. The abnormally dilated wall typically is weakened and susceptible to rupture. Aneurysms can occur in blood vessels such as in the abdominal aorta where the aneurysm generally extends below the renal arteries distal to or toward the iliac arteries.

In treating an aneurysm with a stent-graft, the stent-graft typically is placed so that one end of the stent-graft is situated proximal to or upstream of the diseased portion of the vessel and the other end of the stent-graft is situated distal to or downstream of the diseased portion of the vessel. In this manner, the stent-graft extends through and spans the aneurysmal sac and extends beyond the proximal and distal ends thereof to replace or bypass the dilated wall. The graft material typically forms a blood impervious lumen to facilitate endovascular exclusion of the aneurysm.

Such prostheses can be implanted in an open surgical procedure or with a minimally invasive endovascular approach. Minimally invasive endovascular stent-graft use is preferred by many physicians over traditional open surgery techniques where the diseased vessel is surgically opened, and a graft is sutured into position bypassing the aneurysm. The endovascular approach, which has been used to deliver stents, grafts, and stent-grafts, generally involves cutting through the skin to access a lumen of the vasculature. Alternatively, lumenar or vascular access may be achieved percutaneously via successive dilation at a less traumatic entry point. Once access is achieved, the stent-graft can be routed through the vasculature to the target site. For example, a stent-graft delivery catheter loaded with a stent-graft can be percutaneously introduced into the vasculature (e.g., into a femoral artery) and the stent-graft delivered endovascularly across the aneurysm where it is deployed.

When using a balloon expandable stent-graft, balloon catheters generally are used to expand the stent-graft after it is positioned at the target site. When, however, a self-expanding stent-graft is used, the stent-graft generally is radially compressed or folded and placed at the distal end of a sheath or delivery catheter and self expands upon retraction or removal of the sheath at the target site. More specifically, a delivery catheter having coaxial inner and outer tubes arranged for relative axial movement therebetween can be used and loaded with a compressed self-expanding stent-graft. The stent-graft is positioned within the distal end of the outer tube (sheath) and in front of a stop fixed to the distal end of the inner tube. Regarding proximal and distal positions referenced herein, the proximal end of a prosthesis (e.g., stent-graft) is the end closest to the heart (by way of blood flow path) whereas the distal end is the end furthest away from the heart during deployment. In contrast, the distal end of a catheter is usually identified as the end that is farthest from the operator, while the proximal end of the catheter is the end nearest the operator (handle). Once the catheter is positioned for deployment of the stent-graft at the target site, the inner tube is held stationary and the outer tube (sheath) withdrawn so that the stent-graft is gradually exposed and expands. An exemplary stent-graft delivery system is described in U.S. patent application Publication No. 2004/0093063, which published on May 13, 2004 to Wright et al. and is entitled Controlled Deployment Delivery System, the disclosure of which is hereby incorporated herein in its entirety by reference.

Although the endovascular approach is much less invasive, and usually requires less recovery time and involves less risk of complication as compared to open surgery, there can be concerns with alignment of asymmetric features of various prostheses in relatively complex applications such as one involving branch vessels. Branch vessel techniques have involved the delivery of a main device (e.g., a graft or stent-graft) and then a secondary device (e.g., a graft or stent-graft) through a fenestration or side opening in the main device and into a branch vessel.

The procedure becomes more complicated when more than one branch vessel is treated. One example is when an aortic abdominal aneurysm is to be treated and its proximal neck is diseased or damaged to the extent that it cannot support a patent connection with a prosthesis. In this case, grafts or stent-grafts have been provided with fenestrations or openings formed in their side wall below a proximal portion thereof. The fenestrations or openings are to be aligned with the renal arteries and the proximal portion is secured to the aortic wall above the renal arteries.

To ensure alignment of the prostheses fenestrations and branch vessels, current techniques involve placing guidewires through each fenestration and branch vessel (e.g., artery) prior to releasing the main device or prosthesis. This involves manipulation of multiple wires in the aorta at the same time, while the delivery system and stent-graft are still in the aorta. In addition, an angiographic catheter, which may have been used to provide detection of the branch vessels and preliminary prosthesis positioning, may still be in the aorta. Not only is there risk of entanglement of these components, a standard off the shelf prosthesis with pre-formed fenestrations may not properly align with the branch vessels due to differences in anatomy from one patient to another. A custom prostheses having preformed fenestrations or openings based on a patient's CAT scans also is not free from risk. A custom prosthesis is still subject to a surgeon's interpretation of the scan and may not result in the desired anatomical fit. Further, relatively stiff catheters are used to deliver grafts and stent-grafts and these catheters can change or distort the path or shape of the vessel (e.g., artery) in which they are introduced. When the vessel is reshaped by an outside force such as a stiff catheter, even a custom designed prosthesis may not properly align with the branch vessels.

U.S. Pat. No. 5,617,878 to Taheri discloses a method comprising interposition of a graft at or around the intersection of major arteries and thereafter, use of intravenous ultrasound or angiogram to visualize and measure the point on the graft where the arterial intersection occurs. A laser or cautery device is then interposed within the graft and used to create an opening in the graft wall at the point of the intersection. A stent is then interposed within the graft and through the created opening of the intersecting artery.

U.S. patent application Ser. No. 11/276,512 to Marilla, entitled Multiple Branch Tubular Prosthesis and Methods, filed Mar. 3, 2006, and co-owned by the assignee of the present application, discloses positioning in an endovascular prosthesis an imaging catheter (intravenous ultrasound device (IVUS)) having a device to form an opening in the side wall of the prosthesis. The imaging catheter detects an area of the prosthesis that is adjacent to a branch passageway (e.g., a renal artery), which branches from the main passageway in which the prosthesis has been deployed. The imaging catheter opening forming device is manipulated or advanced to form an opening in that area of the prosthesis to provide access to the branch passageway. The imaging catheter also can include a guidewire that can be advanced through the opening.

Generally speaking, one challenge in prosthesis (e.g., stent-graft) delivery/placement in the vicinity of one or more branch vessels is identifying and locating the position of branch vessels (e.g., arteries). For example, this challenge exists whether the distal end of the prosthesis is to be positioned below or above the renal arteries. Although fluoroscopy has been used to identify branch vessels such as the renal arteries for assisting in prosthesis positioning, there remain challenges with this approach. More specifically, fluoroscopy has been used to observe real time X-ray images of the openings within cardiovascular structures such as the renal arteries during a stent-graft procedure. This approach requires one to administer a radiopaque substance, which generally is referred to as a contrast medium, agent or dye, into the patient so that it reaches the area to be visualized (e.g., the renal arteries). A catheter can be introduced through the femoral artery in the groin of the patient and endovascularly advanced to the vicinity of the renals. The fluoroscopic images of the transient contrast agent in the blood, which can be still images or real time motion images, allow two-dimensional visualization of the location of the renals.

The use of X-rays, however, requires that the potential risks from a procedure be carefully balanced with the benefits of the procedure to the patient. While physicians always try to use low dose rates during fluoroscopy, the length of a procedure may be such that it results in a relatively high absorbed dose to the patient. Patients who cannot tolerate contrast enhanced imaging or physicians who must reduce radiation exposure need an alternative approach for defining the vessel configuration and branch vessel location.

There remains a need to develop and/or improve prosthesis deployment apparatus and methods for endoluminal or endovascular applications.

SUMMARY OF THE INVENTION

The present invention involves improvements in prosthesis deployment apparatus and methods.

In one embodiment according to the invention, a method of real time monitoring the position of a portion of a second vessel, which branches from a first vessel in a human patient comprises acquiring a multi-dimensional data set of a portion of first and second vessels where the second vessel branches from the first vessel; securing at least one marker to the first and second vessels in the vicinity of the second vessel branches from the first vessel; determining the position of the marker in real time; and updating the position of a portion of the three-dimensional data set relative to the juncture between the first and second vessels in real time based on change in position of the marker.

In another embodiment according to the invention, a method of real time monitoring the position of a portion of a second vessel, which branches from a first vessel in a human patient comprises positioning a trackable marker (e.g., an electromagnetic coil) in a second vessel, which branches from a first vessel in a human patient; subjecting the marker to non-ionizing radiation energy (e.g., generating electromagnetic fields about the coil); and processing the marker's response to or effect on the non-ionizing energy (e.g., processing signals from an electromagnetic coil marker in response to electromagnetic field generation thereabout) to determine the position of the marker.

In another embodiment according to the invention, a method of real time virtual three-dimensional modeling of a vessel comprises positioning each of a plurality of trackable markers (e.g., electromagnetic coils) against the inner wall of a vessel; subjecting the markers to non-ionizing radiation energy (e.g., generating electromagnetic fields about the markers); and processing the markers' response to or effect on the non-ionizing radiation (e.g. processing signals from electromagnetic coil markers in response to electromagnetic field generation thereabout) to create a virtual three-dimensional model of a portion of the vessel inner wall.

In another embodiment according to the invention, a method of generating a representation generally along the central axis of a portion of a vessel comprises positioning a plurality of markers in a vessel in a configuration that has an axis that extends generally along the central axis of a portion of the vessel; subjecting the markers to non-ionizing radiation energy; and generating a virtual three-dimensional model of the configuration axis that extends generally along the central axis of a portion of the vessel based on the markers' response to or effect on the non-ionizing radiation energy.

In another embodiment according to the invention, a method of generating a representation generally along the central axis of a portion of a vessel comprises positioning a plurality of electromagnetic coils in a vessel in a configuration that has an axis that extends generally along the central axis of a portion of the vessel; generating electromagnetic fields about the markers; and processing signals from the coils to create a virtual three-dimensional model of the configuration axis that extends generally along the central axis of a portion of the vessel.

In another embodiment according to the invention, a method of forming an opening in a prosthesis, having a tubular wall, in vivo, comprises forming a target in a second vessel that branches from a first vessel in a human patient; endovascularly positioning a prosthesis having a tubular wall in the second passageway such that it overlaps the opening of the second vessel that opens to the first vessel; positioning a puncture device, having a distal end portion and a proximal end portion, in the prosthesis; aligning the distal end portion of the puncture device with the target; and advancing the distal end portion of the puncture device through a portion of the tubular wall toward the target.

In another embodiment according to the invention, a method of forming an opening in a prosthesis, having a tubular wall, in vivo, comprises positioning at least one marker in a second vessel that branches from a first vessel in a human patient; endovascularly positioning a tubular prosthesis in the first vessel such that it overlaps the opening of the second vessel that opens to the first vessel; subjecting the marker to non-ionizing radiation energy; determining the position of the marker based on its response to or effect on the non-ionizing radiation energy; and forming an opening in the prosthesis adjacent to the second vessel opening based on the determined position.

In another embodiment according to the invention, a method of forming an opening in a prosthesis, having a tubular wall, in vivo, comprises positioning at least one electromagnetic coil in a second vessel that branches from a first vessel in a human patient; endovascularly positioning a tubular prosthesis in the first vessel such that it overlaps the opening of the second vessel that opens to the first vessel; generating an electromagnetic field about the coil; processing signals from the coil to determine the position of the coil; and forming an opening in the prosthesis adjacent to the second vessel opening based on the determined position.

In another embodiment according to the invention, an angiographic catheter for locating a branch vessel comprises an elongated member having a perforated distal end portion and a proximal end portion and being adapted for endovascular advancement through a portion of a patient's vasculature, at least one trackable marker (e.g., an electromagnetic coil) secured to the distal end portion for transmitting signals to signal processing apparatus when exposed to electromagnetic fields.

In another embodiment according to the invention, an endovascular system for locating a branch vessel position comprises a first elongated member having a distal end portion and a proximal end portion and being adapted for endovascular advancement through a portion of a patient's vasculature; at least one trackable element (e.g., a sensing coil) secured to the distal end portion; a second elongated member having a distal end portion and a proximal end portion and being adapted for endovascular advancement through a portion of a patient's vasculature; and at least one trackable element (e.g., a sensing coil) being secured to the second elongated member distal end portion.

In another embodiment according to the invention, an endovascular device comprises an elongated member having a distal end portion and a proximal end portion and being adapted for endovascular advancement through a portion of a patient's vasculature, the distal end portion having a memory set configuration and a deformed configuration; and a sheath slidably disposed about the distal end portion and restraining the distal end portion in the deformed state, the sheath being movable to expose the distal end portion and allow the distal end portion to move toward the memory set configuration.

In another embodiment according to the invention, a prosthesis delivery system comprises a prosthesis delivery catheter; a tubular prosthesis disposed in the delivery catheter; an elongated member having a distal end portion and a proximal end portion and being adapted for endovascular advancement through a portion of a patient's vasculature; at least one marker arranged along the distal end portion; a steerable puncture catheter having a proximal end portion and a distal end portion, and a piercing end adapted to pierce graft material; and at least one marker attached to the distal end portion of said steerable catheter.

In another embodiment according to the invention, prosthesis delivery apparatus comprises a guidewire for endovascular delivery in a patient; and trackable marker (e.g., an electromagnetic coil) secured to the guidewire (e.g., at the distal end of the guidewire).

Other features, advantages, and embodiments according to the invention will be apparent to those skilled in the art from the following description and accompanying drawings.

BRIEF DESCRIPTION OF THE DRAWINGS

FIG. 2 diagrammatically illustrates a device extending from one vessel into another.

FIG. 3 depicts one display mode that can be used with the navigation system of FIG. 1 illustrating a display of the device and vessels of FIG. 2.

FIG. 4 depicts another display mode that can be used with the navigation system of FIG. 1.

FIG. 5 depicts yet another display mode that can be used with the navigation system of FIG. 1.

FIG. 9A depicts the marker or sensing apparatus positioned prior to prosthesis deployment, FIG. 9B depicts the marker or sensing apparatus after prosthesis deployment, FIG. 9C illustrates delivering a puncture device to a side wall area of the prosthesis; FIG. 9D depicts fenestration of a side wall area of the prosthesis to perfuse a branch vessel, and FIG. 9E depicts widening the fenestration for receipt of secondary prosthesis.

FIG. 10A depicts the marker or sensing apparatus positioned prior to prosthesis deployment and FIG. 10B depicts the marker or sensing apparatus after prosthesis deployment.

FIG. 16A illustrates the catheter adjacent to material to be punctured, FIG. 16B illustrates the catheter needle penetrated through the material, and FIG. 16C illustrates the opening in the material widened with a tubular dilator and a guidewire extended from the needle for deployment at a desired site.

DETAILED DESCRIPTION

Figure 1:
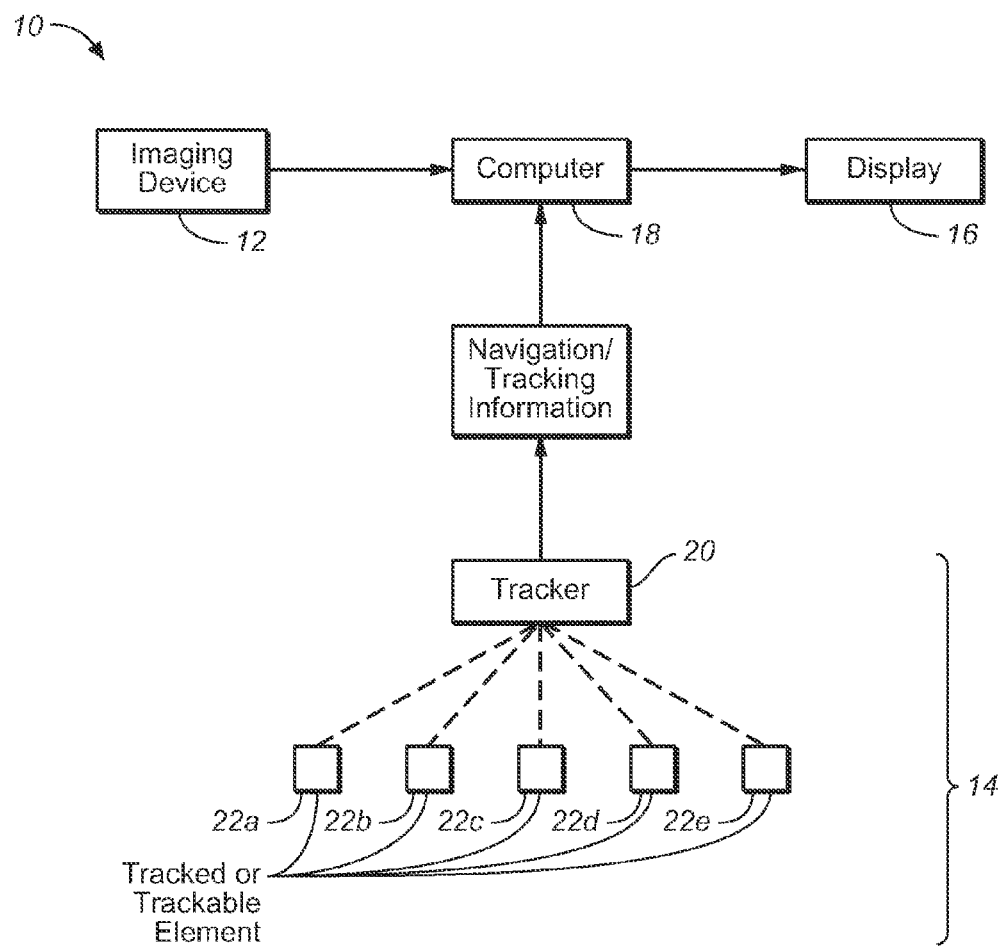
FIG. 1 diagrammatically illustrates one configuration of a navigation system according to one embodiment according to the invention.

The following description will be made with reference to the drawings where when referring to the various figures, it should be understood that like numerals or characters indicate like elements.

Regarding proximal and distal positions, the proximal end of a prosthesis (e.g., stent-graft) is the end closest to the heart (by way of blood flow path) whereas the distal end is the end furthest away from the heart during deployment. In contrast, the distal end of a catheter is usually identified as the end that is farthest from the operator, while the proximal end of the catheter is the end nearest the operator. Therefore, the prosthesis (e.g., stent-graft) and delivery system proximal and distal descriptions may be consistent or opposite to one another depending on delivery path and prosthesis (e.g., stent-graft) location.

Embodiments according to the invention facilitate determining the location, configuration, and/or orientation of a vessel or certain aspects thereof (e.g., a branch vessel), determining the location, configuration and/or orientation of a endovascular devices prior to and during prosthesis deployment as well as the relative position of portions of the vasculature and devices, generating an image model of a portion of one or more vessels (e.g., branch vessels) or devices, and/or formation of one or more openings in a tubular prosthesis in situ to allow branch vessel perfusion when the prosthesis is placed over one or more branch vessels in a patient (e.g., when an aortic abdominal artery stent-graft is fixed to the aorta superior to the renal artery ostia). Branch lumens can occur in or around the intersection of a vessel (e.g., the aorta) and other attendant vessels (e.g., brachiocephalic, anomalous right common carotid originating from the aorta, left common carotid, left subclavian, celiac, superior mesenteric, renal, and inferior mesenteric arteries, and segmentals).

According to various navigation system embodiments described herein, representations of tracked elements and/or surgical devices that are coupled thereto are superimposed on pre-acquired anatomical images in real-time. According to other navigation system embodiments, the navigation system provides the position of one or more surgical devices, anatomical structures, or tracked elements with iconic representations to indicate the relative positions of the devices or tracked elements without the use of patient-specific medical images. And in other embodiments, such iconic representations can be displayed with or superimposed on patient-specific medical images.

"Pre-acquired," as used herein, is not intended to imply any required minimum duration between receipt of the imaging information and displaying the corresponding image. Momentarily storing the corresponding imaging information (e.g., digital signals) in computer memory, while displaying the image (e.g., fluoroscopic image) constitutes pre-acquiring the image. The pre-acquired images can be acquired using fluoroscopic x-ray techniques, CT, MRI, or other known imaging modalities. Representations of surgical or medical devices (e.g., catheters, probes, or prostheses) based on position information acquired from the tracking system can be overlaid on the pre-acquired images of the patient. In this manner, the physician is able to see the location of the surgical device relative to the patient's anatomy.

Referring to FIG. 1, a diagrammatic illustration of one configuration of a navigation system according to one embodiment is shown. In this navigation system, which is generally designated with reference numeral 10, an imaging device 12, tracking system 14, and display 16 are coupled to a computer or processor 18 to display information regarding the position of a tracked element, medical device (e.g., catheter or probe), or the anatomy of a patient, or relative positions between two or more of these objects.

Imaging device 12, which can correspond to a preoperative or intraoperative imaging device, is coupled to computer 18, which stores and processes the data that the imaging device acquires for display on display 16. Many known imaging systems can be used to acquire preoperative or intraoperative data. One example of an imaging system that can be used to acquire preoperative data is a CT scanner, which generates a three dimensional (volumetric) image or model from a plurality of cross-sectional two-dimensional images. Another example of a scanner that can be used to acquire preoperative data is a MR scanner, which also can provide a three dimensional (volumetric) image. Regarding intraoperative data acquisition, navigation using a fluoroscopic two-dimensional system such as the virtual fluoroscopy system described in U.S. Pat. No. 6,470,207, which issued to Simon, et al., can be used. Alternatively, a fluoroscopic three dimensional (volumetric) system such as the O-arm™ imaging system manufactured by Breakaway Imaging Inc. (Littleton, Mass.) can be used as well as other known imaging systems.

Tracking system 14, which measures positions and orientations, and which, for example can be an EM localizer, provides navigational or tracking information to computer 18, which processes that information to locate the position of the tracked element, medical device, instrument, or probe in three dimensional space, which in turn, can be used to help localize patient anatomy such as the ostium of a renal artery.

The tracking system typically comprises a tracker 20 and one or more tracked or trackable elements such as 22a, 22b, 22c, 22d, and 22e, which are coupled to anatomical structures (e.g., the aortic wall) or a medical device (e.g., catheter or probe), to provide the tracking information to computer 18 so that the position of the device and tracked elements in three dimensional space, for example, can be displayed on display 16. Alternatively, an iconic representation of two or more tracked elements and/or medical devices can be displayed with a pre-acquired image or superimposed over a pre-acquired image to illustrate the relative positions thereof to assist the physician in guiding one element relative to (e.g., toward) another. Further, the iconic representations can be displayed without the use of patient-specific medical images as described above.

The tracked elements, examples of which will be described in more detail below, provide position and/or orientation information in one to six degrees of freedom. The tracker comprises a system that provides the position and/or orientation of the tracked elements and sends that tracking information to the computer, which then processes it to ultimately generate a display to the user.

In one embodiment of an electromagnetic field (EMF) based tracking system, the tracker corresponds to a transmitter and the tracked elements (e.g., electromagnetic coils) act as receivers. Alternatively, the tracked elements can correspond to a transmitter and the tracker acts as a receiver. In a radiofrequency based system, the configuration can be the same as in the electromagnetic based system. The tracker can correspond to a transmitter with the tracked elements corresponding to a receiver and vice versa. In a leadless electromagnetic coil based system, the tracker corresponds to a transmitter and receiver and the tracked element(s) corresponds to a reflector or transponder of electromagnetic energy. In an active optical system (an optical system where light-emitting diodes (LEDs) are used), the tracker corresponds to a receiver (camera) and the tracked element corresponds to a transmitter. In a passive optical system (an optical system where retro reflective markers are used), the tracker corresponds to a transmitter and receiver and the tracked element(s) correspond to a reflector of optical energy. And in an ultrasound based system, either configuration can be used, but typically the tracker corresponds to the receiver and the tracked element corresponds to the transmitter. Tracking systems incorporating such elements can operate using non-ionizing radiation.

Referring to FIGS. 2-5, various display modes are shown. Referring to FIG. 2, a catheter 30 or probe is diagrammatically shown extending from a main vessel "V" into a branch vessel "BV1" opposite another branch vessel "BV2". In FIG. 3, two two-dimensional fluoroscopic images illustrate the catheter of FIG. 2 in two different views. FIG. 4 illustrates four intraoperative images of which three illustrate images taken along three different planes (e.g., XYZ planes, which can correspond to the axial, sagittal, and coronal planes) at a location of the main or branch vessel. The fourth image is a three-dimensional image generated from the volumetric data. The images shown in FIG. 4 may be generated from the O-arm™ imaging system described above or they can be acquired preoperatively with a CT, MR, CTA or MRA scanner, for example.

Before overlaying a two-dimensional or three-dimensional pre-procedural or preoperative image with images or graphical representations of tracked elements, a medical device (e.g., catheter or probe) to which the tracked elements are coupled, and/or anatomical structures (e.g., the aortic wall) to which the tracked elements are coupled, the corresponding points in the pre-procedural image and the images or graphical representations are determined. This procedure is generally known as registration of the pre-procedural or preoperative image.

In one example, the preoperative image can be registered via two-dimensional or three-dimensional fluoroscopy. For example, after the preoperative data is acquired, a two-dimensional image is taken intraoperatively and is registered with the preoperative image as is known in the art (see U.S. Patent Publication No. 2004/021571 regarding registering two-dimensional and three dimensional images. The disclosure of U.S. Patent Publication No. 2004021571 is hereby incorporated herein by reference in its entirety). In another example, an O-arm™ imaging system can be used intraoperatively to take a picture/image of the navigation site to be navigated (see, e.g., U.S. Pat. No. 6,6940,941, U.S. Pat. No. 7,001,045, U.S. Patent Publication No. 2004/013225, U.S. Patent Publication No. 2004/0013239, U.S. Patent Publication No. 2004/0170254, and U.S. Patent Publication No. 2004/0179643, the disclosures of which are hereby incorporated by reference in their entirety. Another representative system that performs image registration is described in U.S. Pat. No. 6,470,207 (Simon, et al.), the disclosure of which is hereby incorporated herein by reference in its entirety.

Referring to FIG. 5, an iconic representation of two tracked elements is shown. The image displayed does not correspond to images of the tracked elements, but rather graphics based on information corresponding to the tracked elements position and/or orientation. In the embodiment illustrated in FIG. 5, the intersection of the cross-hairs 40a, 40b, 40c, and 40d can be indicative of (1) tracked elements to be aligned or (2) a computer generated central axis for a portion of a branch artery and an axis formed by two or more tracking elements that are coupled to a medical device as will be described in more detail below, or more generally to any combination of anatomy and portion of one or more devices to be aligned. The iconic representations can be provided continuously in real time to assist the physician in aligning the tracked elements In the illustrative embodiments described hereafter, one or more tracked elements (e.g., signal devices such as magnetically sensitive, electrically conductive sensing coils), are implanted or positioned in one or more vessels, which can include main and/or branch vessels, to determine the position, configuration and/or orientation of the vessel or tracked elements or surgical device(s) as well as relative positions of tracked elements and the vasculature or tracked surgical device(s) and the vasculature. The tracked elements, which also may be referred to as markers can be attached to one or more surgical devices adapted for endovascular delivery to a target site.

In the case of magnetically sensitive, electrically conductive sensing coils, prespecified electromagnetic fields are projected to the portion of the anatomical structure of interest (e.g., that portion that includes all prospective locations of the coils and/or device(s)) in a manner and sufficient to induce voltage signals in the coil(s). Electrical measurements of the voltage signals are sufficient to compute the angular orientation and positional coordinates of the sensing coil(s) and hence the location, configuration and/or orientation of the vasculature and/or devices of interest. An example of sensing coils for determining the location of a catheter or endoscopic probe inserted into a selected body cavity of a patient undergoing surgery in response to prespecified electromagnetic fields is disclosed in U.S. Pat. No. 5,592,939 to Martinelli, the disclosure of which is hereby incorporated herein by reference in its entirety. Another example of methods and apparatus for locating the position in three dimensions of a sensor coil by generating magnetic fields which are detected at the sensor is disclosed in U.S. Pat. No. 5,913,820 to Bladen, et al., the disclosure of which is hereby incorporated herein by reference in its entirety.

Figure 6A:
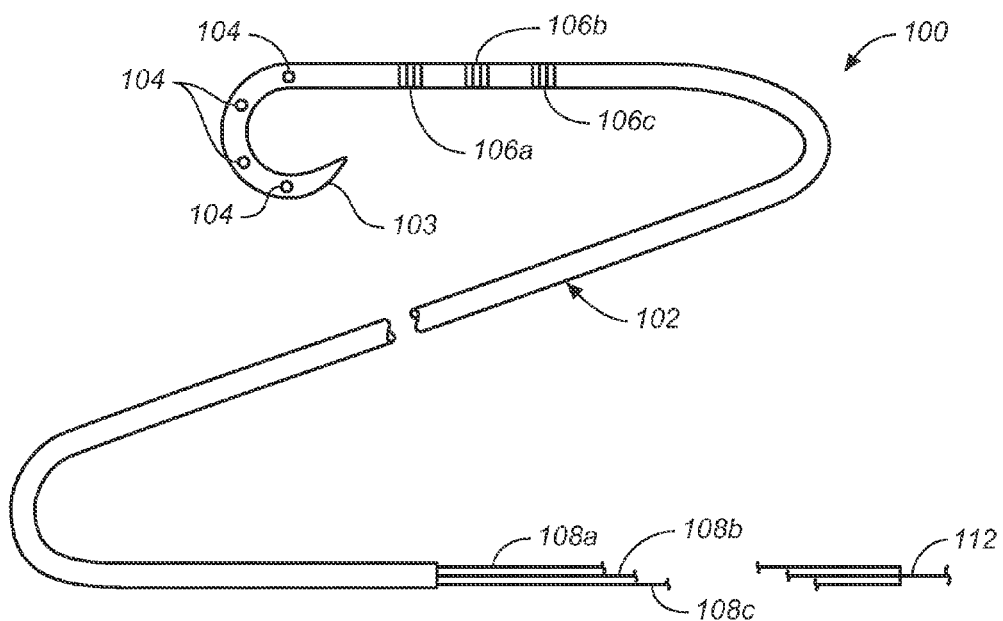
FIG. 6A diagrammatically illustrates one embodiment of marker or sensing apparatus according to the invention.

Referring to FIG. 6A, one system according to the invention is depicted and generally indicated with reference numeral 100. System 100 comprises angiographic catheter 102, which is adapted for endoluminal or endovascular delivery to a target site in a patient. Angiographic catheter 102 includes a distal end portion and a proximal end portion where the proximal end portion is adapted to extend to a conventional handle for manipulation. The distal end portion can include a pig tail 103 having a plurality of openings 104 formed therein for delivering contrast medium to a target site. One or more tracked elements or markers, which are indicated in the illustrative example with reference numerals 106a, 106b, and 106c, are attached to the distal end portion of the catheter by any suitable means.

The tracked elements or markers can be sensors and can be magnetically sensitive, electrically conductive sensing coils as described above. In this case, they also may be referred to as antenna coils. The markers or sensing coils can be wound around the catheter and glued thereto. Alternatively, they can be embedded in the catheter as can any of the tracked elements described herein. In this example, each separate lead or conductor 108a, 108b, and 108c extends from a respective marker 106a, 106b, and 106c through the catheter lumen or along the outer surface thereof for coupling to a signal processing circuit, an example of which will be described in more detail below. The leads can extend through an intermediate cable bundle sheath 112, which extends to the processing circuit.

Angiographic catheters typically are used during prosthesis (e.g., stent-graft) implantation to deliver contrast medium for fluoroscopy. With an angiographic catheter constructed according to the invention (e.g., angiographic catheter 102), the catheter can be restrained against the vessel (e.g., aortic artery) wall by the implanted prosthesis. The markers that are attached to the catheter's distal end portion can be secured against the vessel wall to provide real time anatomic markers for a portion of the vessel wall (e.g., a portion of the aorta). The tracked elements or markers can provide reference points for the local anatomy. When the vasculature of interest is tortuous and a relatively rigid branch vessel prosthesis deployment catheter is introduced to the target site, the presence of the branch vessel prosthesis deployment catheter and its pressing on the luminal walls may reshape or displace the vasculature at the target site. This can change the position of the branch vessels as compared to what has been detected in pre-procedural imaging or mapping (e.g., fluoroscopy). The real time data that the markers provide can be processed to generate real time tracking information, which can be used as a basis to generate a virtual image of a portion of the main vessel from which the branch vessel or vessels branch. This image can be registered with pre-acquired information of the main and branch vessel(s) to generate an image of the juncture between the branch vessel(s) and the main vessel.

Figure 6B:
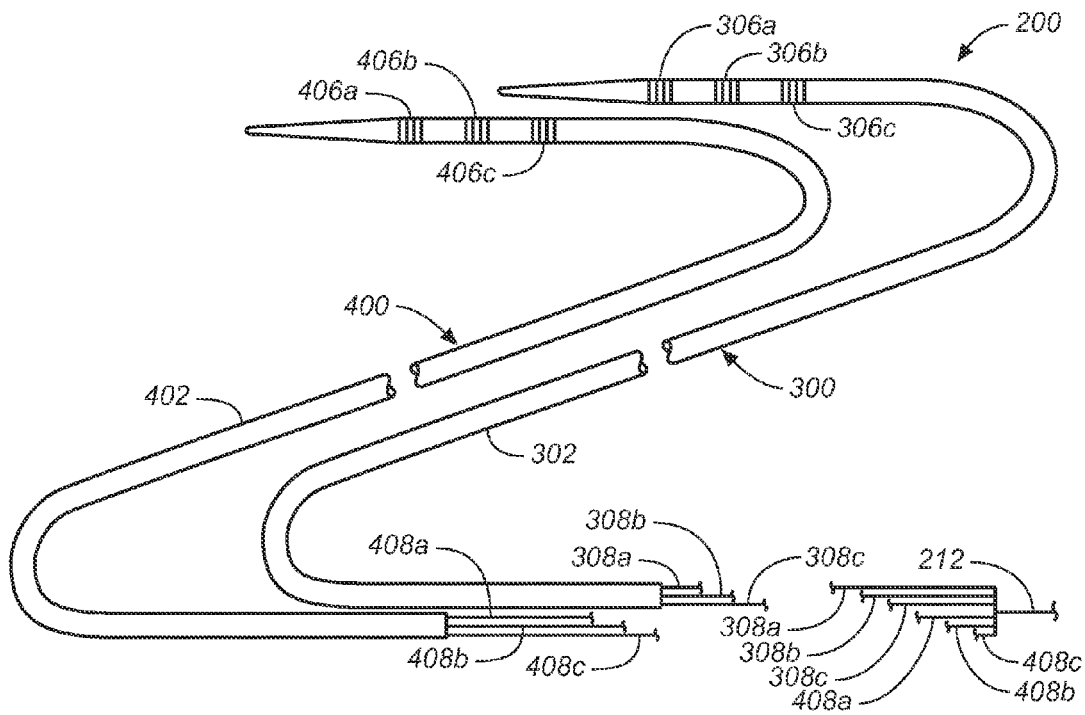
FIG. 6B diagrammatically illustrates one embodiment of marker or sensing apparatus according to the invention.

Alternatively, endoluminal/endovascular marker or sensor positioning apparatus such as the apparatus shown in FIG. 6B can be used to temporarily position tracked elements or markers such as sensors in a branch vessel such as an aortic branch vessel, which includes the brachiocephalic, anomalous right common carotid originating from the aorta, left common carotid, left subclavian, celiac, superior mesenteric, renal, inferior mesenteric, and segmental branches, prior to deployment of the prosthesis (e.g., stent-graft) to mark the location of the branch vessel and provide real time data about the branch vessel position and orientation as the prosthesis is deployed. This can provide assistance with alignment of a prosthesis having one or more preformed fenestrations formed in its side with one or more branch vessels. In the alternative, the markers can be used to assist with the process of in situ fenestration of the prosthesis as will be discussed in more detail below.

Referring to FIG. 6B, a system for positioning tracked elements or markers in multiple branches is shown and generally designated with reference numeral 200. System 200 comprises marker positioning devices 300 and 400, each adapted for endoluminal or endovascular delivery to a target site in a patient.

Apparatus 300 comprises an elongated member 302, which can be in the form of a catheter (e.g., microcatheter) or a guidewire. Elongated member 302 has a distal end portion and a proximal end portion that is adapted to extend to a conventional handle for operator manipulation. One or more markers (e.g., sensing coils or signal devices as described above), generally indicated in the illustrative example with reference numerals 306a, 306b, and 306c, are attached to the distal end portion of elongated member 302 by any suitable means as described above in regard to markers 106a, 106b, and 106c. Therefore, the markers also can be magnetically sensitive, electrically conductive sensing coils. Each separate lead or conductor 308a, 308b, and 308c extends from a respective marker 306a, 306b, and 306c through cable bundle sheath 212 to a signal processing circuit, an example of which will be described in more detail below. In the case where elongated member 302 is a catheter, the leads can extend through the catheter lumen or along the outer surface of the catheter. In the case where elongated member 302 is a guidewire, the leads extend along the outer surface thereof and can be spirally wound thereabout.

Apparatus 400 comprises an elongated member 402, which can be in the form of a catheter (e.g., microcatheter) or a guidewire. Elongated member 402 includes a distal end portion and a proximal end portion that is adapted to extend to a conventional handle for operator manipulation. One or more markers (e.g., sensing coils or signal devices as described above), generally indicated in the illustrative example with reference numerals 406a, 406b, and 406c, are attached to the distal end portion of elongated member 402 by any suitable means as described above in regards to markers 106a, 106b, and 106c. Therefore, the markers also can be magnetically sensitive, electrically conductive sensing coils. Each separate lead or conductor 408a, 408b, and 408c extends from a respective marker 406a, 406b, and 406b for coupling through cable bundle sheath 212 to a signal processing circuit, an example of which will be described in more detail below. In the case where elongated member 402 is a catheter, the leads can extend through the catheter lumen or along the outer surface of the catheter. In the case where elongated member 402 is a guidewire, the leads extend along the outer surface thereof and can be spirally wound thereabout.

The tracked devices or markers in the embodiments depicted in FIGS. 6A and 6B can be equidistantly spaced or nonequidistantly spaced along the longitudinal axis of any of the devices 102, 302, and 402. The spacing typically depends on the use and rigidity of the elongated member. For example, closer spacing typically is used when the elongated member will be significantly bent in the region of the markers during use to enhance the accuracy of representation of the elongated member on the display (closer spacing would result in a more accurate representation—in contrast—equidistant spaced markers which are far apart, could have accuracy that is poor). The number of markers attached to catheter 102 also can vary. In general, at least one marker having at least three degrees of freedom is required to provide the position and orientation of the portion of the elongated member or catheter to which the marker is attached. Additional position and orientation data of the elongated member or catheter can be generated from pre-acquired measurements thereof. On the other hand, when the distal portion of the elongated member may undergo significant bending, it may be desirable to include two or three spaced markers. For example, if one knows the bending or flexure properties of the catheter or elongated member so that one can generally predict how a portion of the catheter or elongated member between two markers attached thereto will bend when the two markers are moved closer to one another and if one also knows the distance between the two markers when the portion is in a straight line configuration, an estimated virtual image of the bent catheter can be generated. A third marker placed midway between the other two markers can indicate the apex of the curved portion if the portion of the catheter or elongated member between the outer markers bends uniformly throughout its length.

Although a system comprising two catheters or guidewires, which can be especially advantageous when it is desired to place markers in two different vessels such as the renal arteries, has been described, a single system having a single catheter or guidewire or a system having more than two catheters or guidewires can be used depending on the application.

Figure 7:
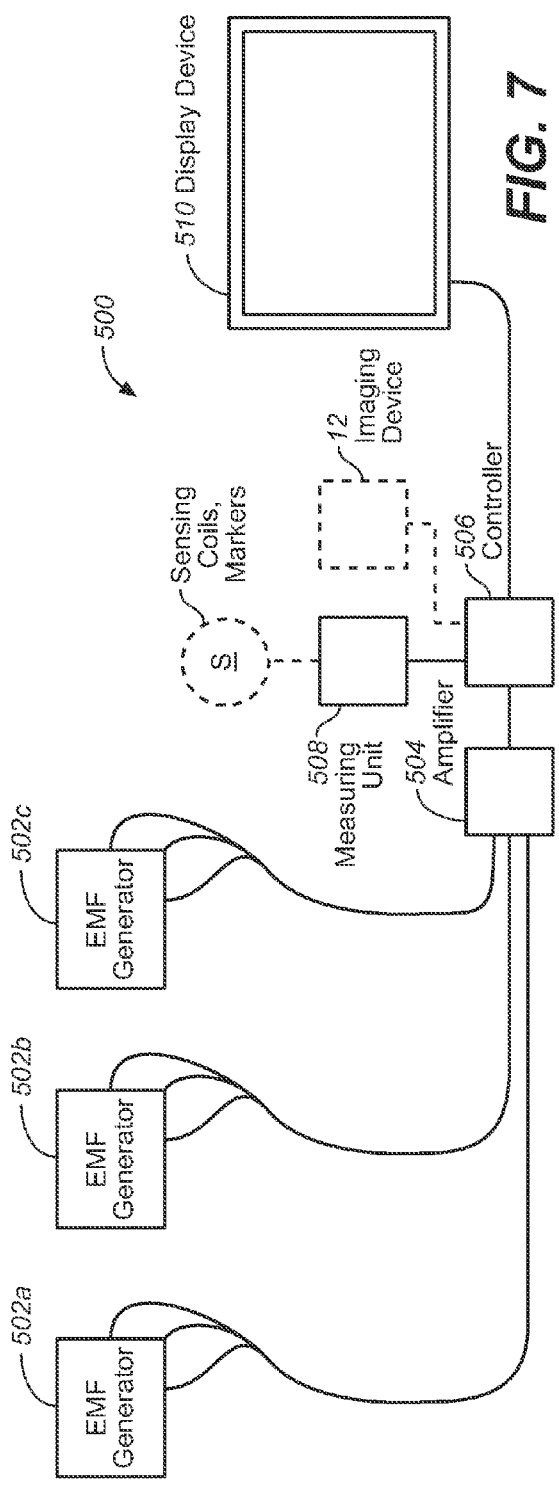
FIG. 7 diagrammatically illustrates field generating and signal processing apparatus for use with the marker or sensing apparatus described herein.

In the example where the markers are magnetically sensitive, electrically conductive sensing coils (e.g., antenna coils), any suitable electromagnetic field generating and signal processing circuit or circuits for locating the position in three dimensions of the markers can be used (see e.g., U.S. Pat. No. 5,913,820 to Bladen, et al. (supra)). One such field generating and signal processing circuit configuration for generating magnetic fields at the location of markers 106a-c, 306a-c, and 406a-c when the markers are magnetically sensitive, electrically conductive sensing coils "S", and processing the voltage signals that the sensor type markers generate in response to the generated magnetic fields is shown in FIG. 7 and generally designated with reference numeral 500. Although nine coils are shown in three groups of three in the example depicted in FIG. 7, it should be understood that nine separate coils can be used. More generally, the product (multiplication) of the number of receiver coils and the number of transmitter coils must equal at least 9. So for example, it is possible to have 3 transmitter coils and 3 receiver coils to measure 6 degrees of freedom.

In the illustrated example, circuit 500 generally includes three electromagnetic field (EMF) generators 502a, 502b, and 502c, amplifier 504, controller 506, measurement unit 508, and display device 510. Each field generator comprises three electrically separate coils of wire (generating coils) wound about a cuboid wooden former. The three coils of each field generator are wound so that the axes of the coils are mutually perpendicular. The nine generating coils are separately electrically connected to amplifier 504, which is able, under the direction of controller 506, to drive each coil individually.

In use, controller 506 directs amplifier 504 to drive each of the nine generating coils sequentially. Once the quasi-static field from a particular generating coil is established, the value of the voltage induced in each sensing coil by this field (e.g., markers 22a-22e (FIG. 1)) is measured by the measurement unit 508, processed and passed to controller 506, which stores the value and then instructs the amplifier 504 to stop driving the present generating coil and to start driving the next generating coil. When all generating coils have been driven, or energized, and the corresponding nine voltages induced into each sensing coil have been measured and stored, controller 506 calculates the location and orientation of each sensor relative to the field generators and displays this on a display device 510. This calculation can be carried out while the subsequent set of nine measurements are being taken. Thus, by sequentially driving each of the nine generating coils, arranged in three groups of three mutually orthogonal coils, the location and orientation of each sensing coil can be determined.

The sensor and generating coil specifications, as well as the processing steps are within the skill of one of ordinary skill of the art. An example of coil specifications and general processing steps that can be used are disclosed in U.S. Pat. No. 5,913,820 to Bladen, et al., the disclosure of which is hereby incorporated herein by reference in its entirety.

Figure 8:
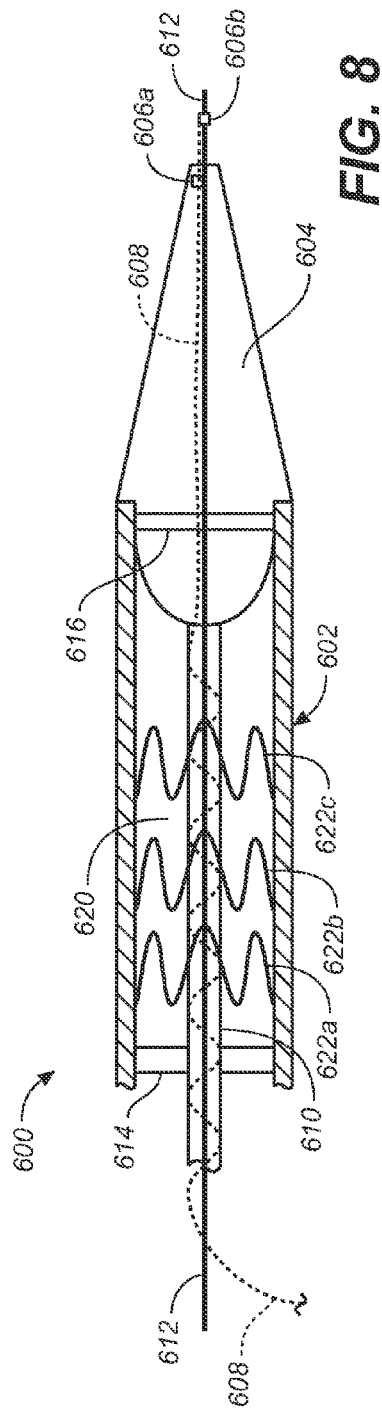
FIG. 8 illustrates a schematic cross sectional view of one prosthesis delivery catheter system with optional sensing devices.

Referring to FIG. 8, one loaded prosthesis delivery system according to the invention is shown and designated with reference numeral 600. When the prosthesis to be delivered is a self-expanding graft or stent-graft (such as stent-graft 620, it is generally radially compressed or folded and placed in the distal end portion of the delivery catheter and allowed to expand upon deployment from the catheter at the target site as will be described in detail below.

Prosthesis delivery system 600 comprises catheter tube or sheath 602 (outer tube) and inner guidewire tube 610, which are coaxial and arranged for relative axial movement therebetween. Guidewire 612 can be inserted into guidewire tube 610 so that the system can be tracked thereover to the desired site. The prosthesis (e.g., stent-graft 620, which can include a plurality of undulating stent elements 622a, 622b, and 622c to support the tubular graft material as is known in the art) is positioned within the distal end of the outer tube 602 and in front of pusher member or stop 614, which is concentric with and secured to inner guidewire tube 610 and can have a disk or ring shaped configuration with a central access bore to provide access for guidewire tube 610. A radiopaque ring 616 can be provided on the proximal end of obturator 604 (tapered tip) or the inside of sheath 602 to assist with imaging the obturator or distal end of sheath 602 using fluoroscopic techniques. Once the catheter is positioned for deployment of the prosthesis at the desired site, the inner member or guidewire lumen 610 with stop 614 are held stationary and the outer tube or sheath 602 withdrawn so that obturator 604 is displaced from sheath 602 and the stent-graft gradually exposed and allowed to expand. Stop 614 therefore is sized to engage the distal end of the stent-graft as the stent-graft is deployed. The proximal ends of the sheath 602 and inner tube or guidewire lumen 610 are coupled to and manipulated by handle (not shown). Obturator 604 optionally can be configured with a cavity to receive the proximal portion of the stent-graft so that the operator can allow expansion of the stent-graft proximal end during the last phase of its deployment. In this regard, any of the stent-graft deployment systems described in U.S. patent application Publication No. 2004/0093063, which published on May 13, 2004 to Wright et al. and is entitled Controlled Deployment Delivery System, the disclosure of which is hereby incorporated herein by reference in its entirety by reference, can be incorporated into stent-graft delivery system 600.

Prosthesis delivery system 600 can include optional tracked element or marker 606a, which, for example, can be an antenna coil type sensor, and a lead (not shown), which extends from marker 606a through guide tube 610 to field generating and signal processing circuit 500 to facilitate determining the position of marker 606a and/or the distal end of the obturator. Alternatively, optional marker 606b, which can be an antenna coil can be provided on guidewire 612. In this case, lead 608 extends from sensor 606b through guide tube 610 to field generating and signal processing circuit 500 to facilitate determining the position of marker 606b and/or the distal end of the guidewire.

Undulating stent elements 622a, 622b, and 622c can be secured to the inner or outer wall of the tubular graft material (which can comprise, for example, Dacron® or expanded polytetrafluoroethylene (ePTFE)). The stent-graft also can include an undulating support wire secured to the inner or outer wall of the proximal portion of the tubular graft and a bare spring secured to the proximal portion of the tubular graft as is known in the art. The proximal end of the bare spring typically flares outward to enhance stent-graft anchoring. Sutures or any other suitable means can be used to secure the stents, support wire, and bare spring to the graft material.

The following examples are provided for illustrative purposes only. It should be understood that the order of the text does not necessarily indicate the order of any of the procedural steps in any of the examples as will be apparent from reading the examples.

EXAMPLE 1

Referring to FIGS. 9A-E, an exemplary operation of system 100 where the tracked elements or markers used are sensing coils and more specifically electromagnetic field (EMF) coils will now be described. For the purposes of the example, the procedure involves the endovascular delivery and deployment of an AAA bifurcated stent-graft in the vicinity of the renal arteries. In the example described below, the procedure can be performed using a preprocedural or intraoperative scan of the vasculature being navigated to generate a three-dimensional model of the navigational path. An exemplary preprocedural scan approach will be described first and an intraoperative scan approach will follow.

Pre-Procedural or Preoperative Scan

First or Pre-Procedural Scan and Aortic Data Acquisition:
Prior to the surgical procedure, the patient is scanned using either a CT, CTA, MRI, or MRA scanner to generate a three-dimensional model of the vasculature to be tracked. The abdominal aorta and branch vessels of interest (e.g., renal arteries) are scanned and images taken therealong to create a three-dimensional pre-procedural data set for that vasculature and create a virtual model upon which real time data will be overlaid.

Magnetic Field Generator Placement:
The three magnetic field generators 502a, 502b, and 502c are fixed in a predetermined position so that the spatial relationship between the field generator coils and the sensing coils can be determined. Alternatively, nine separate field generating coils can be used instead of magnetic field generators 502a, 502b, and 502c as described above (FIG. 7). Other numbers of generating coils also can be used as described above and as would be apparent to those skilled in the art. In a further alternative, the field generating coils can be attached or mounted to the imaging device.

Deliver Marker(s) to the Desired Site:
The patient is prepared for surgery and a cut is made down to a femoral artery. Angiographic catheter 102 is endovascularly advanced to a position in the vicinity of (e.g., at, above, or below) the renal arteries (FIG. 9A) using conventional fluoroscopic techniques.

Figure 9A:
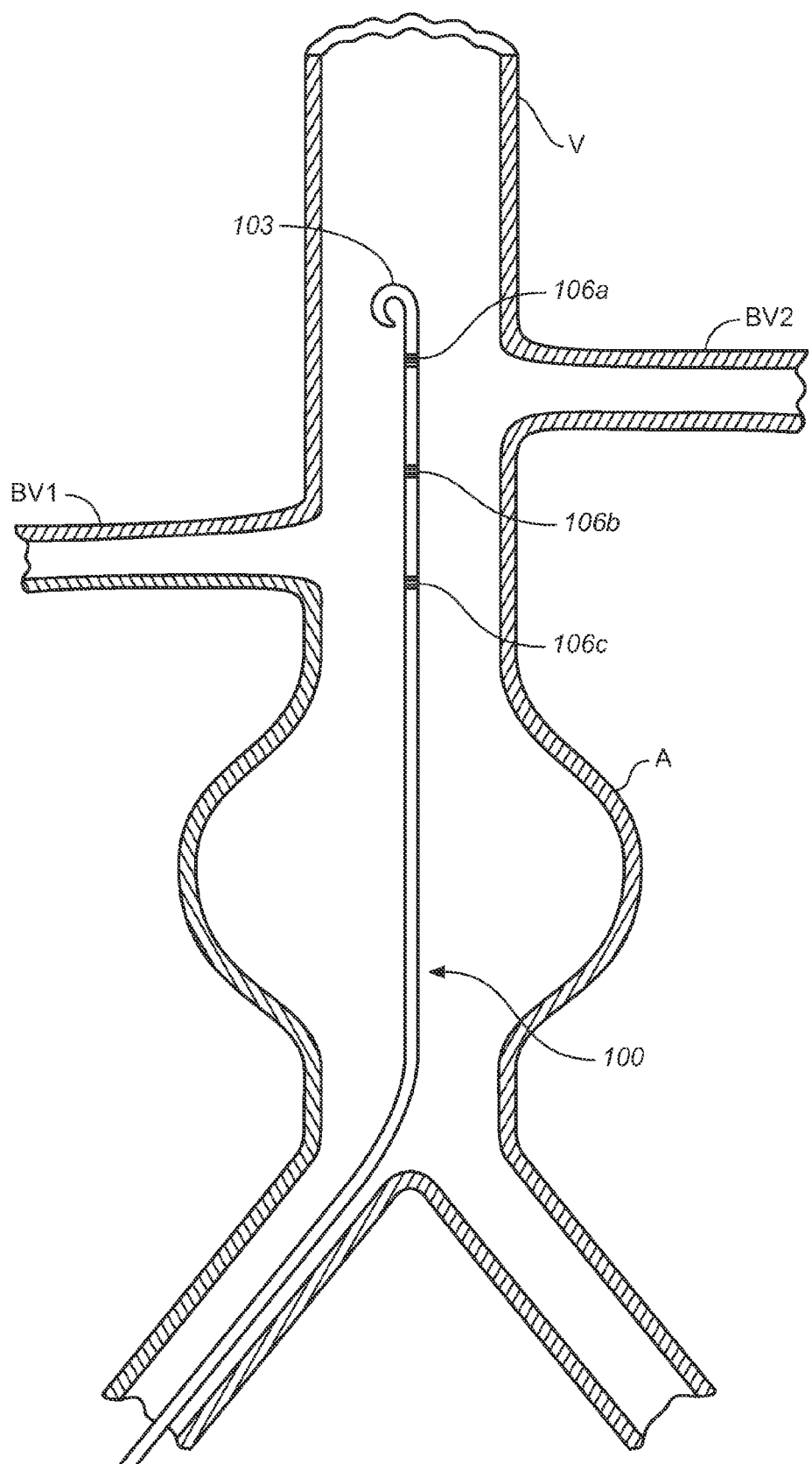
FIGS. 9A-E which are schematic cross sectional views, diagrammatically illustrate use of the embodiment of FIG. 6A; where
Figure 9B:
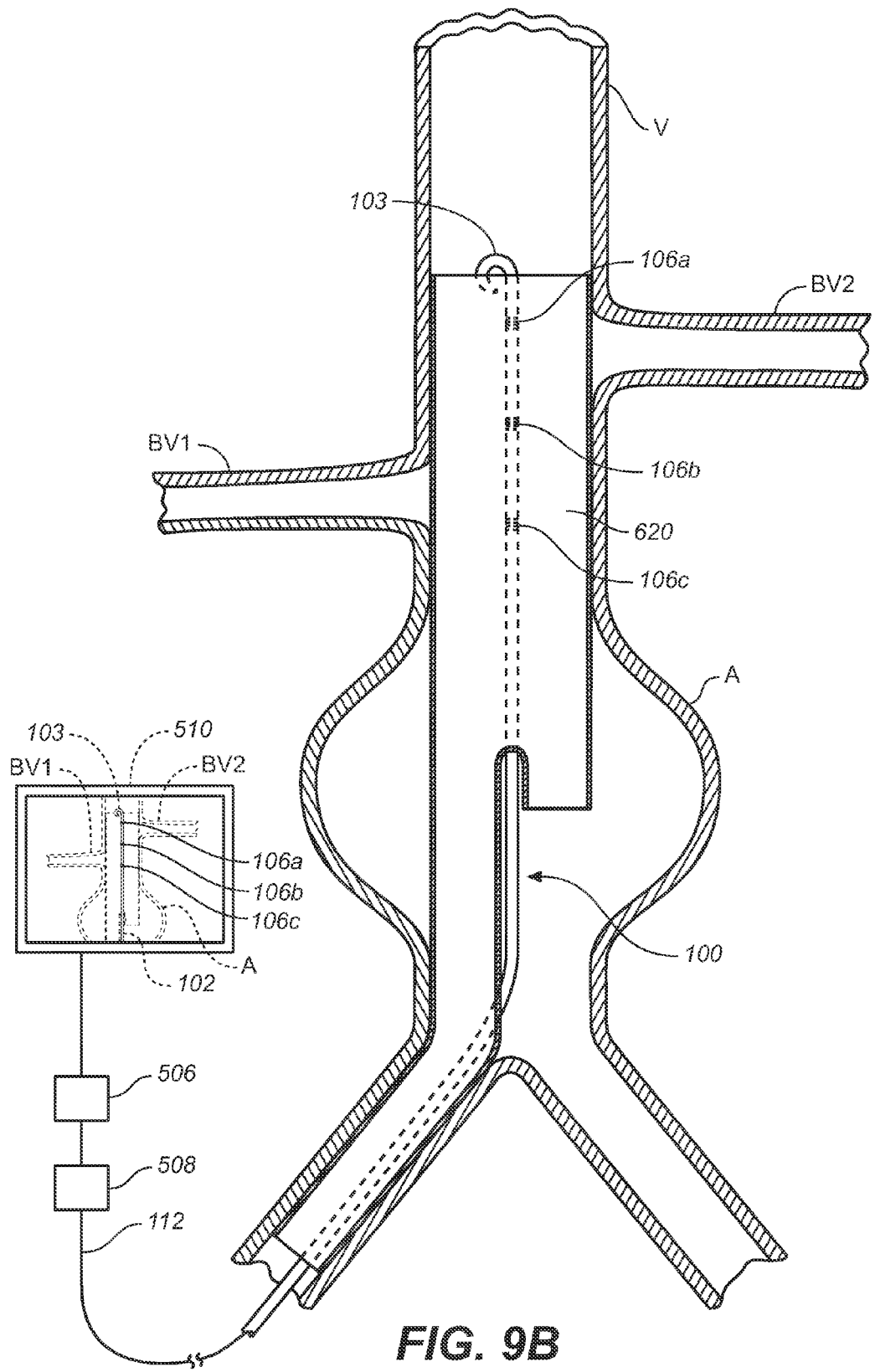

Marker Securement to the Anatomy:
Referring to FIG. 9B, the operator deploys stent-graft 600 as shown with angiographic catheter 102 disposed between the stent-graft and aortic wall with the stent-graft pinning the angiographic catheter and its marker or sensors 106a, 106b, and 106c against the aortic wall. The stent-graft is positioned for deployment using conventional fluoroscopic techniques.

Second or Intraoperative Scan and Aortic Data Acquisition:
Two or more two-dimensional fluoroscopic X-rays are taken or other imaging techniques used to obtain a two-dimensional data set of the aorta. Alternatively, a three-dimensional data set of the aorta can be acquired. The three-dimensional pre-procedural scan is then registered with the secondary two-dimensional data sets or the secondary three-dimensional data set. The registration is based on the similar anatomical or vascular features that were subject to the pre-procedural and intraoperative (secondary) scans used to generate the data sets and can be done using known registration techniques. One registration approach for registering a three-dimensional data set to a two dimensional data set is described in U.S. Patent Publication No. 2004/0215071 to Frank, et al, the disclosure of which is hereby incorporated herein by reference in its entirety Creating a Dynamic Reference:
During acquisition of the secondary or intraoperative data set, the field generators are actuated and signals received from the angiographic catheter coils 106a, 106b, and 106c to provide a "dynamic reference" for the anatomy (e.g., the aorta). The registration of the first and second data sets is computed and subsequently referenced to the coordinate system attached to the marker or coils (as noted in other places herein, the markers are secured to the aorta, renals or other parts of the anatomy using one or more methods for creating a "rigid" attachment between the markers and the anatomy. Once this affixment has been performed, it is now possible to define a fixed coordinate system relative to the markers (and therefore the underlying anatomy) which moves together with any motion in the anatomy. Therefore, any registrations which are computed either between the anatomy and the pre-operative or intra-operative images are also referenced to this anatomy-referenced coordinate system. This allows the registration transformation to compensate for any motion of the anatomy) the marker referencing process that is carried out by processor 18 or controller 506. That is, the coils establish the coordinate system. Since the markers are secured to the aorta, the coordinate system is fixed relative to the anatomy and in this case the aorta. This allows real time updating of the pre-procedural data set and corresponding image when the coil positions are determined in real time. Processor or computer 18 or controller 506 manipulates the data to move the image acquired from the pre-procedural scan based on coil movement so that the physician can monitor movement of the renal ostium or ostia as the aorta moves. This is helpful when the pre-procedural position of the renal arteries changes due to, for example, patient movement resulting from the patient's heart beat, respiration or other function and allows the pre-procedural scan to be updated to reflect that change and/or movement in real time. The real time display can be used to assist the physician in monitoring the position of one or both of the renal arteries and puncture the stent-graft at a location adjacent thereto. It also should be understood that the dynamic marker(s) can be associated with either data set, but the first data set may be more valuable since the branch vessels (e.g., renal arteries) may be covered by the stent-graft during the second data set acquisition.

Localization:
In order to obtain the position and orientation of the coils, a first electromagnetic field coil is energized as described above. The value of the voltage induced in angiographic antenna coil 106a is measured by measurement unit 508, processed and passed to controller 506, which stores the value and then instructs the amplifier 504 to stop driving the present generating coil and to start driving the next generating coil. When all nine generating coils have been driven, or energized, and the corresponding nine voltages induced into the coil have been measured and stored, controller 506 calculates the location and orientation of the sensor relative to the field generators and displays a graphical representation of this on a display device 510. This process is then carried out for sensor 106b and sensor 106c.

When the positional data of sensors 106a, 106b, and 106c is acquired, it used to establish a fixed coordinate system attached to the anatomy, a real time image of the renal ostia can be displayed to provide a target for puncturing the stent-graft adjacent thereto.

Figure 9C:
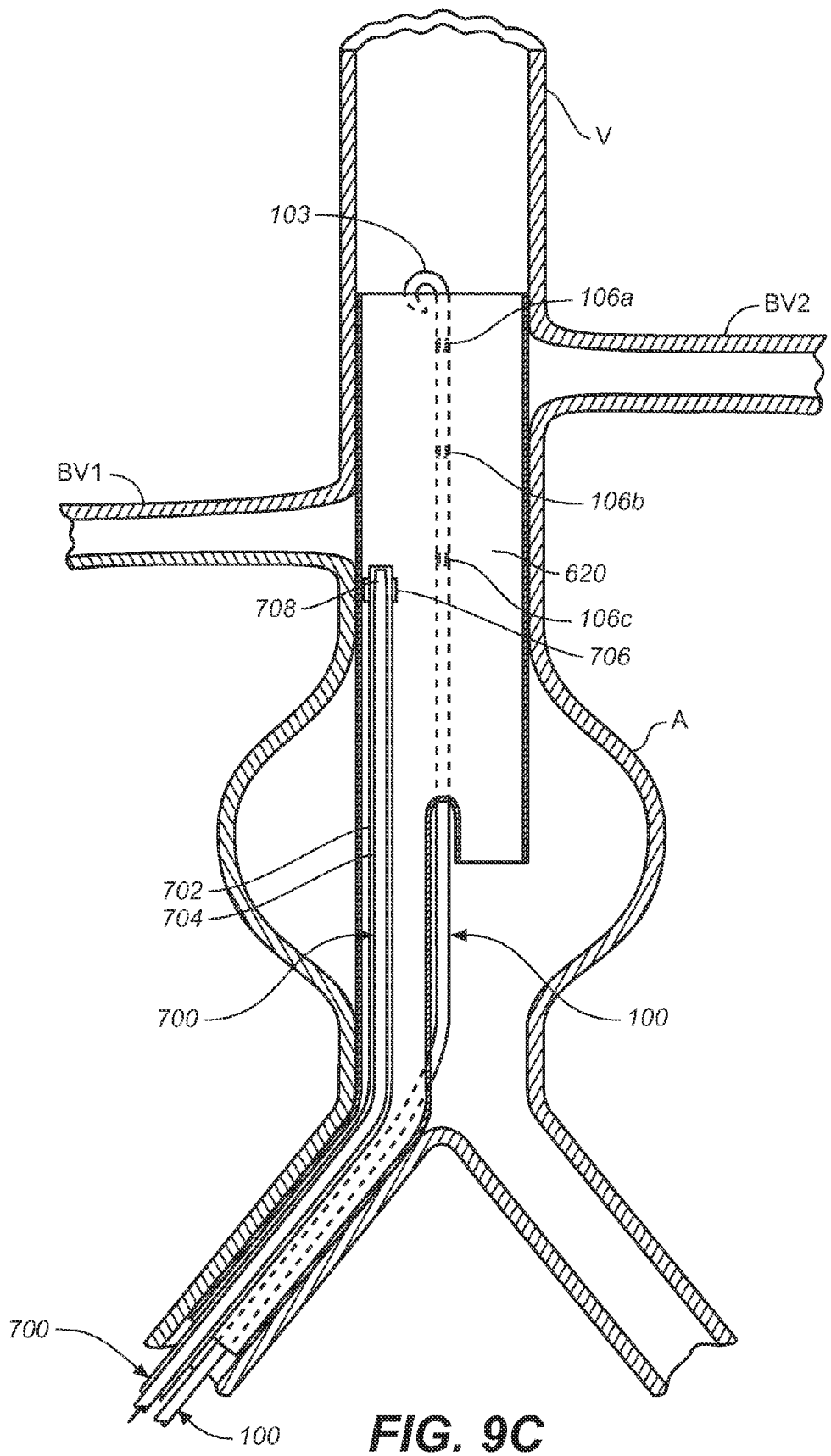

Puncture Catheter Delivery:
Referring to FIG. 9C, a steerable puncture catheter 700 is advanced through the aorta to one of the renal arteries (e.g., branch vessel BV1). A marker on the puncture catheter provides a beacon to iconically represent on the display and track the movement of the puncture catheter toward the selected branch vessel or a portion of the stent-graft adjacent to the selected branch vessel. The updated image of the aorta based on images acquired while the renal arteries were uncovered provides an updated image of one or more branch vessel ostia (e.g., one or both renal arteries) to which the puncture catheter marker(s) is guided. Alternatively, an image of the catheter can be overlaid on an image of the aorta that is generated from either the first or second data sets.

In one embodiment, puncture catheter 700 has a steerable outer tube or guide catheter 702, an inner tube 704 slidably disposed in outer tube 702, and one or more tracked elements or markers 706 (e.g., one or more sensor or antenna coil) attached to the distal end portion of outer tube 702. Markers 706 can be adhesively secured to the outer surface or inner surface of the catheter or they can be embedded in the distal end portion of outer tube 702. The distal end portion 708 of inner tube 704 is tapered or frustoconically shaped to serve as a widener or dilator as it is passed through the opening made with the puncture catheter. A hollow needle or piercing member 710 is slidably disposed in inner tube 704 and dimensioned to allow a guidewire such as guidewire 712 (FIG. 9E) to pass therethrough and out from it's distal beveled piercing tip, which is configured to pierce the graft material of the stent-graft.

Although the illustrative marker is shown as being attached to outer tube 702 in this example, it should be understood that the marker or markers can be secured or attached to or embedded in the distal end portion of inner tube 704 or needle 710.

Figure 9D:
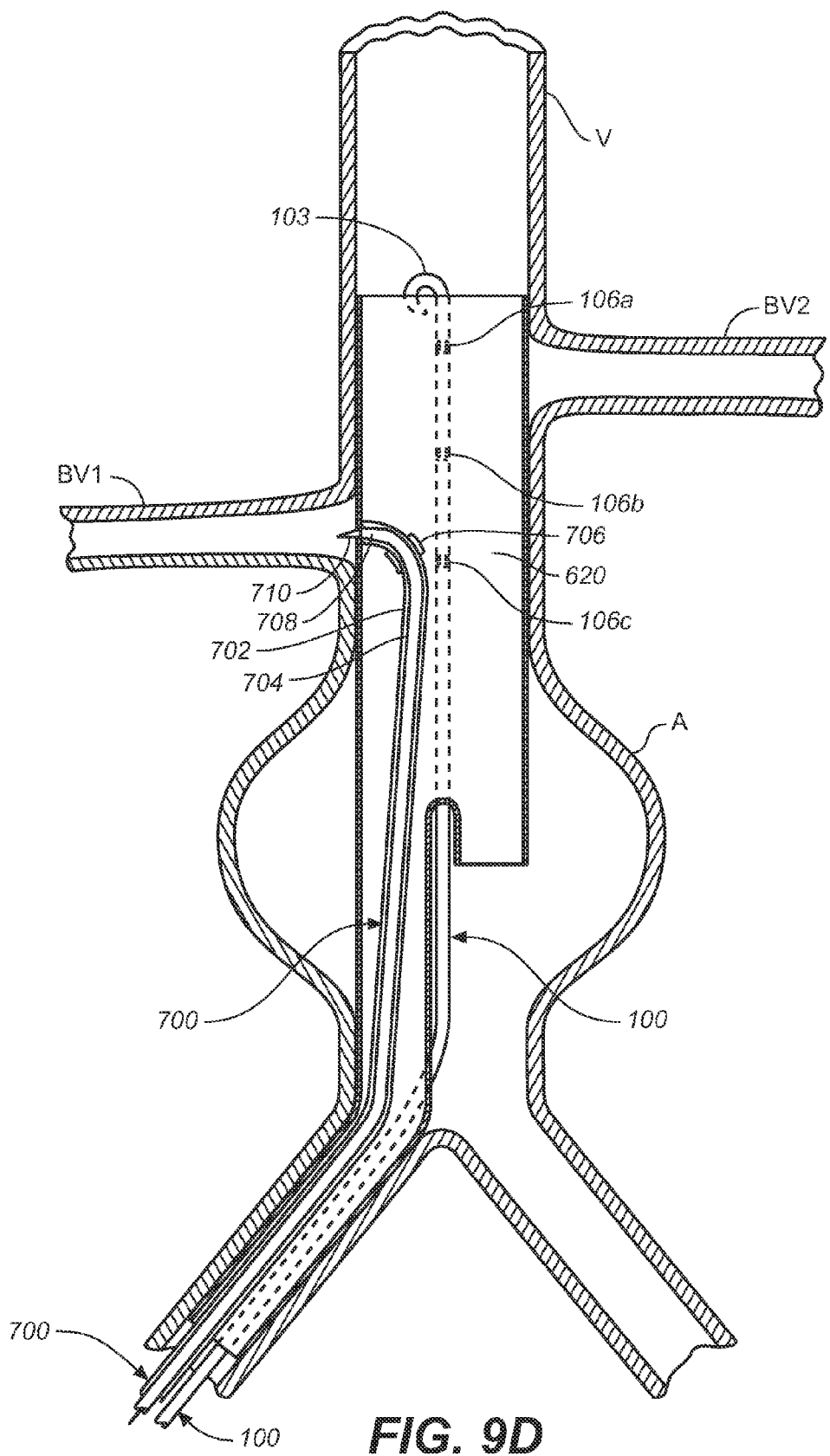

In the exemplary embodiment, the marker 706 is a sensing coil, which transmits signals to circuit 500 in response field generators 502a, 502b and 502c sequentially generating electromagnetic fields thereabout in the same manner as described above. The signals are processed and the position and orientation of sensor 706 calculated after which an image of the sensor is registered with and superimposed over the pre-procedural image on display 510. The display shows the sensor image as it is moved toward the lower renal artery. The display is used to guide the piercing distal tip of needle 710 through the side wall of the stent-graft 620 and into branch vessel BV1, which in this example is the lower renal artery, as shown in FIG. 9D. A virtual image of piercing distal tip of needle 710 also can be created based on dimensional data for catheter 700, which can be programmed into computer or controller 506.

Figure 9E:
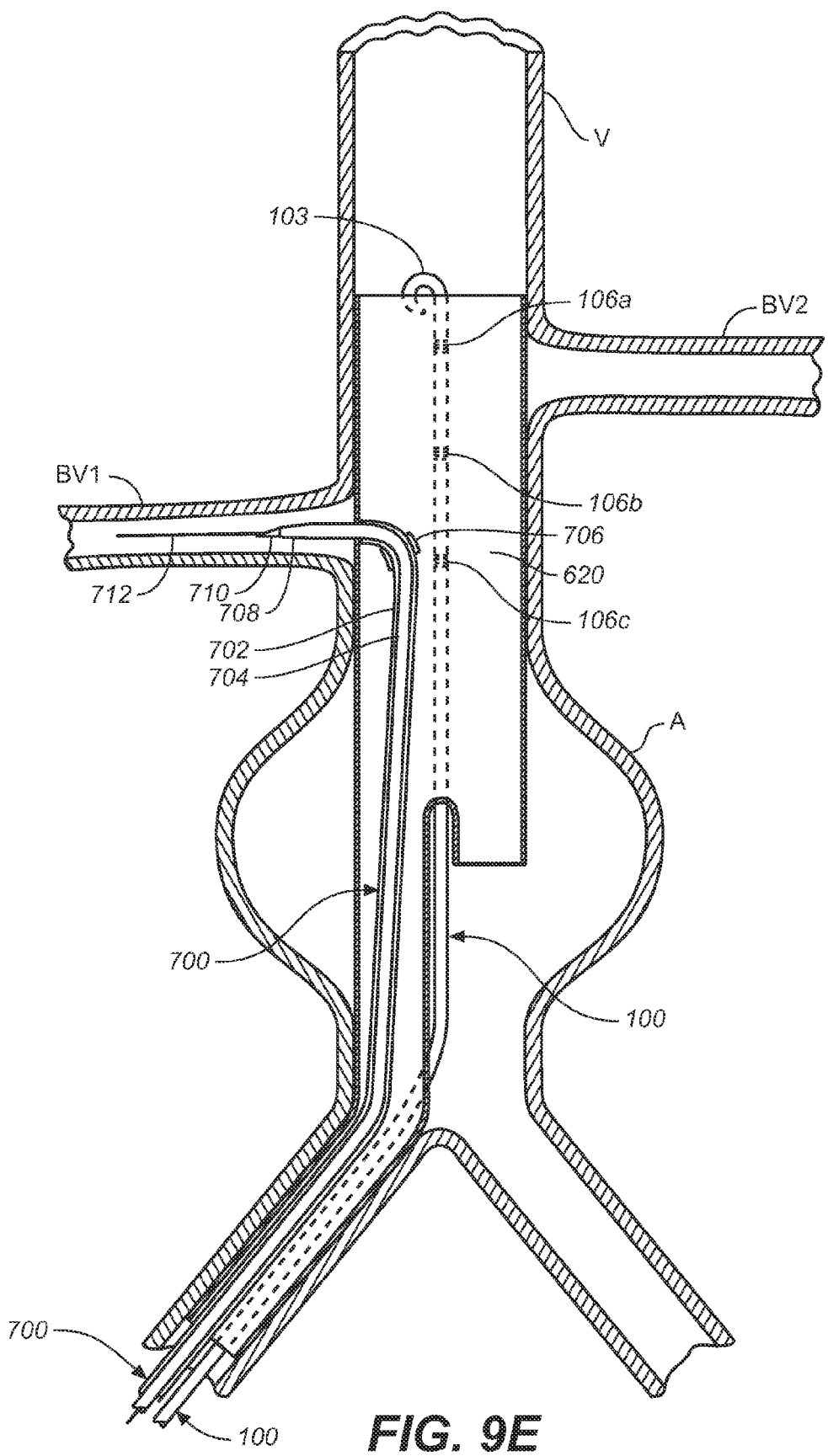

Referring to FIG. 9E, inner tube 704 is moved relative to outer tube 702 so that it is further advanced with its hole widener or dilator portion 708 widening the opening for delivery of a branch vessel stent-graft. Guidewire 712 is deployed from hollow needle 710 as shown and the puncture catheter is then removed with the guidewire in place for tracking a branch vessel stent-graft thereover.

A stent-graft delivery system such as stent-graft delivery system 600 (FIG. 8) (without guidewire 612) is used to deliver a branch stent-graft to one of the renal arteries (e.g., BV1) over guidewire 712.

A similar opening is formed (not shown) in the stent-graft adjacent to the other renal artery before or after deployment of the first branch vessel stent-graft. If the second puncture is made before deployment of the first branch vessel stent-graft, a second guidewire is placed in the same manner as guidewire 712. If the second puncture is made after deployment of the first branch vessel stent-graft, either guidewire 712 or another guidewire can be used. After the second stent-graft is similarly deployed, all catheters are withdrawn.

It should be understood that after establishing the dynamic reference as described above, optional variations in the procedures are contemplated. In one example, the idea is to use "intra-operative" 3D fluoroscopy, not "live" 3D fluoroscopy. The images are acquired solely during the procedure and they are navigated on using the methods described herein.

Intraoperative Scan Approach A

Magnetic Field Generator Placement:

The three magnetic field generators 502a, 502b, and 502c are fixed in a predetermined position as described above so that the spatial relationship between the field generator coils and the sensing coils can be determined. Other numbers of generator coils can be used as described above.

Marker Delivery:

As described above, the patient is prepared for surgery and a cut is made down to a femoral artery and angiographic catheter 102 with marker coils 106a, 106b, and 106c is endovascularly advanced to a position above the renal arteries using conventional fluoroscopic techniques.

Intraoperative Scan and Aortic Data Acquisition:

An intraoperative scan is taken at this time using imaging device 12, for example, to provide a first three-dimensional data set for the abdominal aorta and create a virtual model upon which the real time data from sensor coils 106a, 106b, and 106c can be associated to provide a "dynamic reference" as described above. Any suitable scanner can be used such as the O-arm™ Imaging System described above. Also see U.S. Pat. No. 6,470,207 to Simon, et al., the disclosure of which is hereby incorporated herein by reference in its entirety. Contrast medium can be used to enhance imaging detail.

Marker Securement to the Anatomy:

Catheter 102 is positioned as shown and a stent-graft deployed to pin or secure catheter 102 and marker coils 106a, 106b, and 106c to the aortic wall as described above.

Second Intraoperative Scan and Aortic Data Acquisition:

A second scan is taken to provide a second three-dimensional data set representative of the abdominal aorta and can include data relative to catheter 102 and coils 106a, 106b, and 106c on catheter 102 to register the first data three-dimensional data set with the coils on catheter 102. The first and second data sets are registered with one another as is known in the art for example: once the stent is in place and securing the catheter to the aorta wall, it is no longer possible to acquire contrast images of the renals and flow to the renals is occluded. However, the first image acquire can contain contrast in the renals. The purpose of the $2^{nd}$ scan is to register the $1^{st}$ scan and allow navigation on an image set containing the renals. The reason the first scan can't be used directly is that there is no dynamic reference in place at the time of the initial acquisition. The two scans are registered using intensity image-based techniques. Medtronic Surgical Navigation has a product called "AutoMerge" which performs this functionality. Once these two data sets are merged, it is now possible to navigate on the first data set based on the dynamic reference coordinate system established in the $2^{nd}$ data set. While one could view either the first or second data set, it is more likely that the first would be used since it contains the renals. Note that if it is possible to have a contrast image once the markers are secured to the aorta—then only a single image is necessary and it is not necessary to perform an "AutoMerge". When using the O-arm™ Imaging System, the scanner automatically registers or synchronizes the tracked element or coil representations to the first intraoperative three-dimensional image. This requires that either a transmitter or receiver element of tracking system 14 be physically attached to the imaging system, and that a calibration process be performed either during manufacturing, during each use, or during each image. This calibration process determines the transformation between the coordinate system of the imaging device and the tracker (e.g., tracker or measuring unit 14).

Creating a Dynamic Reference:

During acquisition of the second intraoperative data set, the field generators are actuated and signals received from angiographic catheter coils 106a, 106b, and 106c, which are associated with the first data set, to provide a "dynamic reference" for the anatomy as described above. Alternatively, the markers can be associated with the second data set in this and the previous example. However, the first data set may have more information and provide the desired information base. For example, in the case where the stent-graft is positioned over the renal arteries after acquisition of the first data set, renal artery information has been captured in the first data set so that it can be displayed.

Puncture Catheter Delivery:

Steerable puncture catheter 700 is tracked via marker 706 to the portion of the stent-graft adjacent to the lower renal artery ostium and then used to fenestrate the stent-graft and deploy a guidewire in the renal artery as described above. Its marker can serve as a beacon to guide it toward the displayed updated position of the branch vessel ostium as described above. Alternatively, an image of the catheter can be overlaid on displayed real time images of the aorta that are generated from the updated data set. The opening can be widened before the branch vessel stent-graft is deployed as described above. The portion of the stent-graft adjacent to the other renal artery can be fenestrated and a guidewire and branch vessel stent-graft deployed in the same manner as described above.

Intraoperative Scan Approach B

Magnetic Field Generator Placement:

The three magnetic field generators 502a, 502b, and 502c are fixed in a predetermined position as described above so that the spatial relationship between the field generator coils and the sensing coils can be determined. Other numbers of generator coils can be used as described above.

Marker Delivery:

As described above, the patient is prepared for surgery and a cut is made down to a femoral artery and angiographic catheter 102 with marker coils 106a, 106b, and 106c is endovascularly advanced to a position above the renal arteries using conventional fluoroscopic techniques.

Marker Securement to the Anatomy:

Catheter 102 is positioned as shown and a stent-graft deployed to pin or secure catheter 102 to the aortic wall as described above.

Intraoperative Scan and Aortic Data Acquisition:

A three-dimensional data set representative of the abdominal aorta is acquired and simultaneously associated with coils 106a, 106b, and 106c on catheter 102. Any suitable scanner can be used such as the O-arm™ Imaging System described above. Also see U.S. Pat. No. 6,470,207 to Simon, et al., the disclosure of which is hereby incorporated herein by reference in its entirety.

Creating a Dynamic Reference:

During acquisition of the intraoperative data set, the field generators are actuated and signals received from angiographic catheter coils 106a, 106b, and 106c, which are associated with the data set, to provide a "dynamic reference" for the anatomy as described above.

Puncture Catheter Delivery:

Puncture catheter 700 can be tracked to the region of a target ostium and used to fenestrate the stent-graft and deploy a guidewire in the accompanying renal artery for tracking a stent-graft thereover as described in any of the examples provided above.

EXAMPLE 2

Figure 10A:
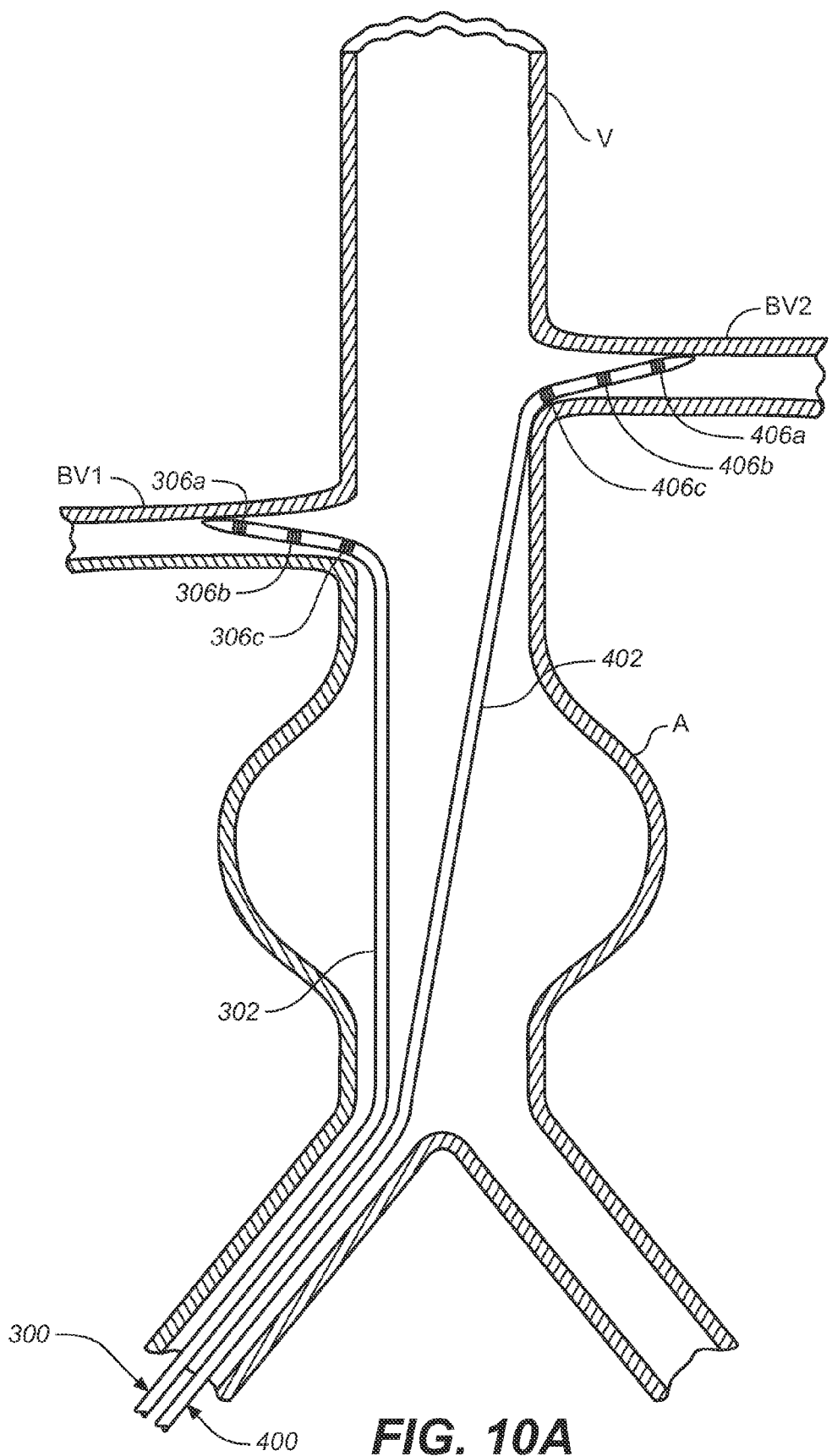
FIGS. 10A and 10B diagrammatically illustrate use of the embodiment of FIG. 6B; where
Figure 10B:
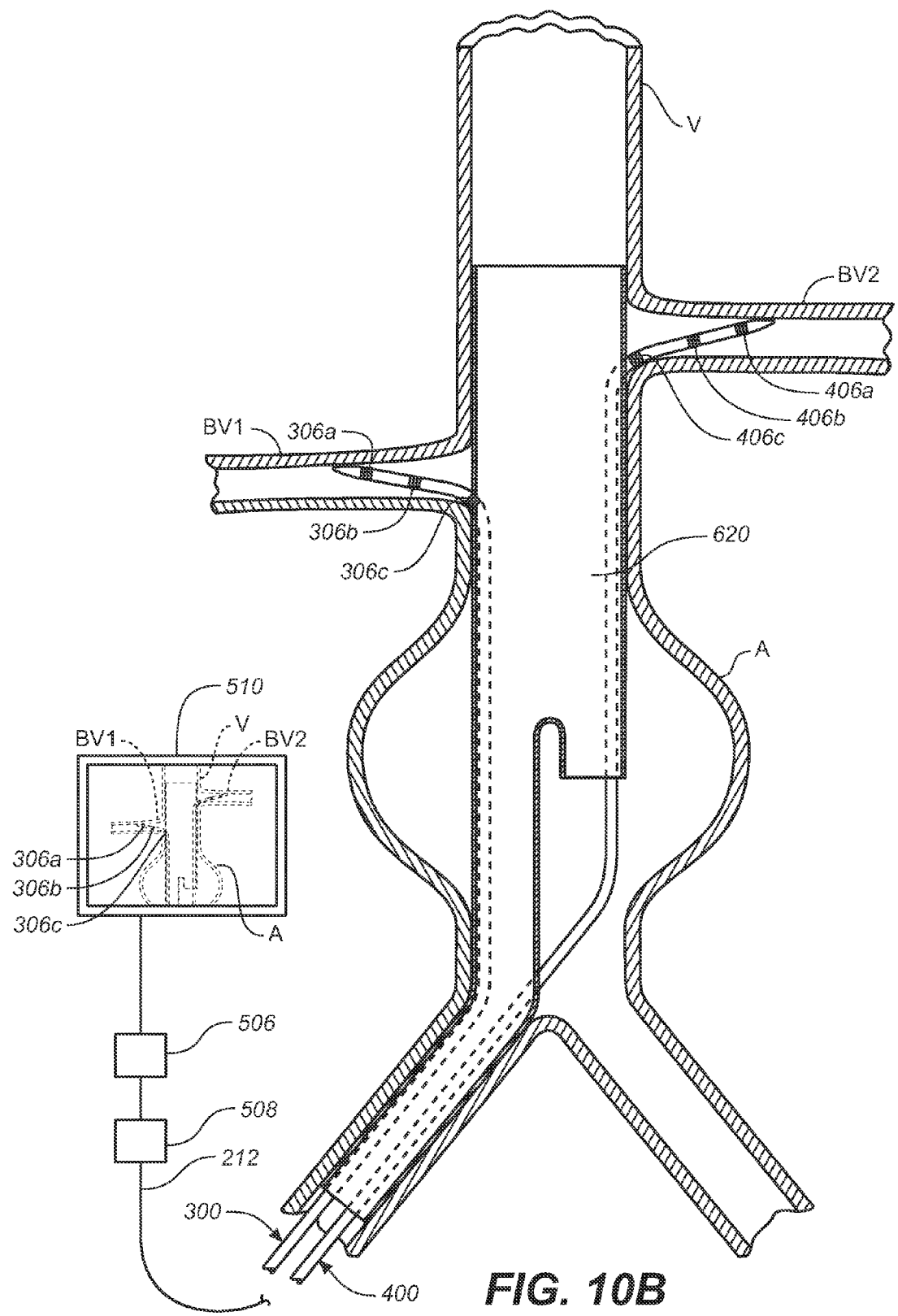

Referring to FIGS. 10A and 10B, a procedure for locating vessels for prosthesis deployment using system 200 where the tracked elements or markers used are sensing coils and more specifically electromagnetic field (EMF) coils will now be described. For the purposes of the example, the procedure involves the endovascular delivery and deployment of an AAA bifurcated stent-graft in the vicinity of the renal arteries.

As described above, the patient is prepared for surgery and a cut is made down to a femoral artery and elongated members 302 and 402 are endovascularly advanced toward the renal arteries and their distal portions positioned in the renals using conventional fluoroscopic techniques (FIG. 10A).

While viewing the fluoroscopic image of the renals and tracked elements or markers 306c and 406c, the markers or sensing coils are aligned with a lower portion of a respective ostium of the renal arteries generally indicated with BV1 and BV2.

In one variation, after sensing coils 306c and 406c are aligned with the renal arteries as described above, a stent-graft delivery system such as system 600 having tracked element or marker 606a is used to guide guidewire 612 of system 600 to one of the renal arteries. Iconic representations of the markers based on data acquired therefrom as described above are displayed on display 510 to monitor the relative positions of marker 606a and either or both marker sets 306a-c or 406a-c to assist in positioning the stent-graft at the desired location.

In a further variation, the stent-graft dimensions are input into controller or computer 506 to create a virtual image of the stent-graft relative to coil 606a to position the stent-graft at the proximal neck of the aneurysm below the renal arteries or to position the stent-graft above one or both renals, as shown in FIG. 10B, depending on the application. Alternatively, the coil sets can be used to create a real time virtual image of the ostia. The real time data generated by stent-graft sensor or coil 606a then can be used to monitor the relative positions of one or more ostium of either or both renal arteries and the stent-graft.

When the stent-graft is positioned with its proximal end above the renal arteries as shown in FIG. 10B, steerable puncture catheter 700 is used to fenestrate the stent-graft. Steerable puncture catheter 700 is advanced through the aorta to one of the renal arteries (e.g., branch vessel BV1) where it is advanced through the side wall of the stent-graft. The position of marker coil 706 of the puncture catheter is monitored as it generates signals in response to the fields generated by the field generator coils as described above that are measured and processed to determine its position and orientation. Controller 506 processes this information and sends the processed information to display 510 where an iconic representation of the fenestration catheter is displayed. Iconic representations of catheter 306a, 306b, and 306c and/or coils 406a, 406b, and 406c are displayed in a similar manner so that the relative position of the puncture catheter marker and a respective microcatheter (or guidewire) marker is displayed for the physician. Alternatively, an iconic representation of the renal arteries can be generated. The idea here is that the location of the catheters fixed in the renals define "targets" for the fenestration catheter. To the extent that these targets accurately represent the desired location of the fenestration catheters—then it is possible to create a computer graphic which represents both the target location (the renal catheters) and the fenestration catheter. The surgeon would align these iconic representations and then assume that the catheter is in the correct location.

Puncture catheter 700 can be tracked to the region of a target ostium and used to fenestrate the stent-graft and deploy a guidewire in the accompanying renal artery for tracking a branch vessel stent-graft thereover. Another fenestration can be similarly formed in the stent-graft to deploy a guidewire in the other branch vessel and track a branch vessel stent-graft thereover.

In one variation, a conventional stent-graft can be deployed with its proximal end above one or both of the branch vessels using conventional fluoroscopic techniques to secure one or both of elongated members 302 and 402 in place with the respective distal portions in the branch vessels. Thereafter, puncture or fenestration catheter 700 is tracked to a portion of the stent-graft to puncture a hole therein adjacent to a respective branch vessel for deployment of a guidewire over which a branch vessel stent-graft can be guided and deployed as described above.

Elongated members 302 and 402 can also be floppy microcatheters similar to flow-directed microcatheters used in the intracranial vasculature. Such catheters will conform to the angle of most if not all renal ostia.

Figure 11A:
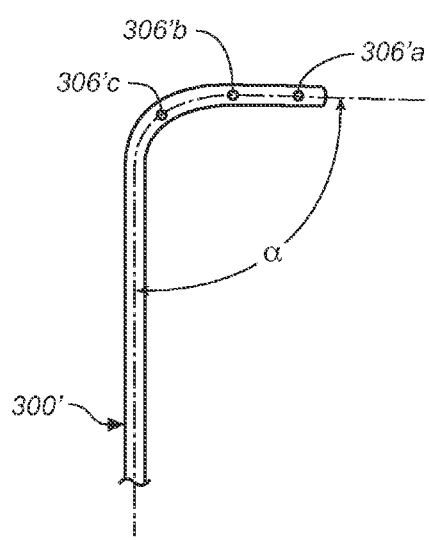
FIG. 11A illustrates another embodiment of marker or sensing apparatus according to the invention.
Figure 11B:
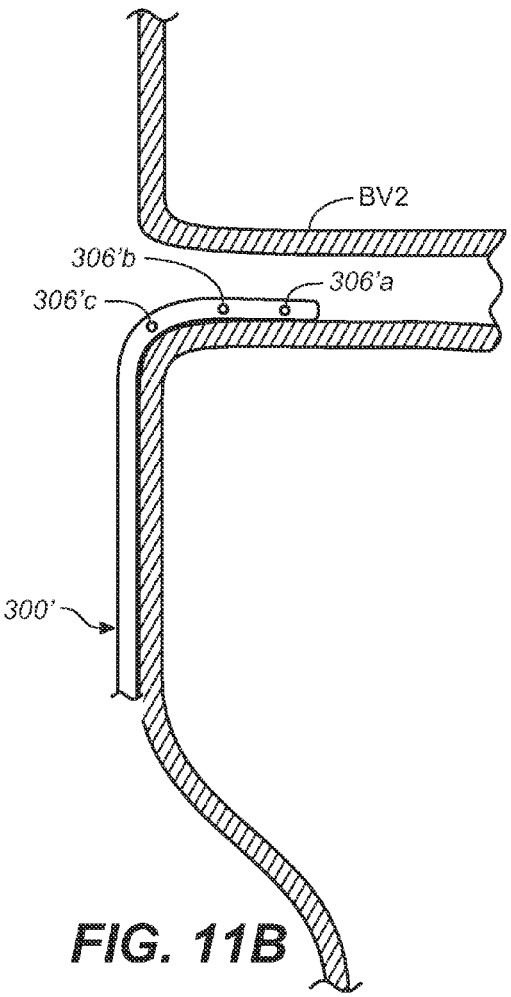
FIG. 11B illustrates the embodiment of FIG. 10A positioned in a branch vessel.

Referring to FIGS. 11A and 11B, a variation of earlier described tracked element or marker positioning device 300 is shown and generally designated with reference numeral 300'. In this embodiment, device 300', which can be in the form of a catheter or guidewire, has a preshaped bend formed therein. In the illustrative example, the catheter or guidewire has an L-shaped configuration. The bend forms an angle α measured between the longitudinal axis of the portion distal to the bend and the longitudinal axis of a portion proximal to the bend. Angle α typically is in the range of about 70-110° and more typically is in the range of about 80-100°, and can be about 90°. In the illustrative example, angle α is 90°. A plurality of tracked elements or markers (e.g., elements 306'a, 306'b, and 306'c, which can be similar or the same as sensors 306a, 306b, and 306c) are attached to the portion that is distal to the bend. With this construction, device 300' can conform to the wall of the vasculature at the juncture of a branch vessel as shown in FIG. 11B with marker 306c providing a point along the ostium of the branch vessel which can identify the position of a known point on the ostium which, in turn, can be used to register the location of the ostium to the tracker (e.g., element 20 in FIG. 1 or element 508 in FIG. 7).

Elements 306'a, 306'b, and/or 306'c also can provide a target for a puncture catheter (e.g., puncture catheter 700) to fenestrate a stent-graft covering the branch vessel in which the sensors are positioned without the need for a pre-acquired image. In this case, iconic representations of the markers 306a, 306b, and/or 306c and puncture catheter marker 706 can be displayed on display 510 to assist the physician in guiding the puncture catheter through the stent-graft and into a target branch vessel.

Figure 12:
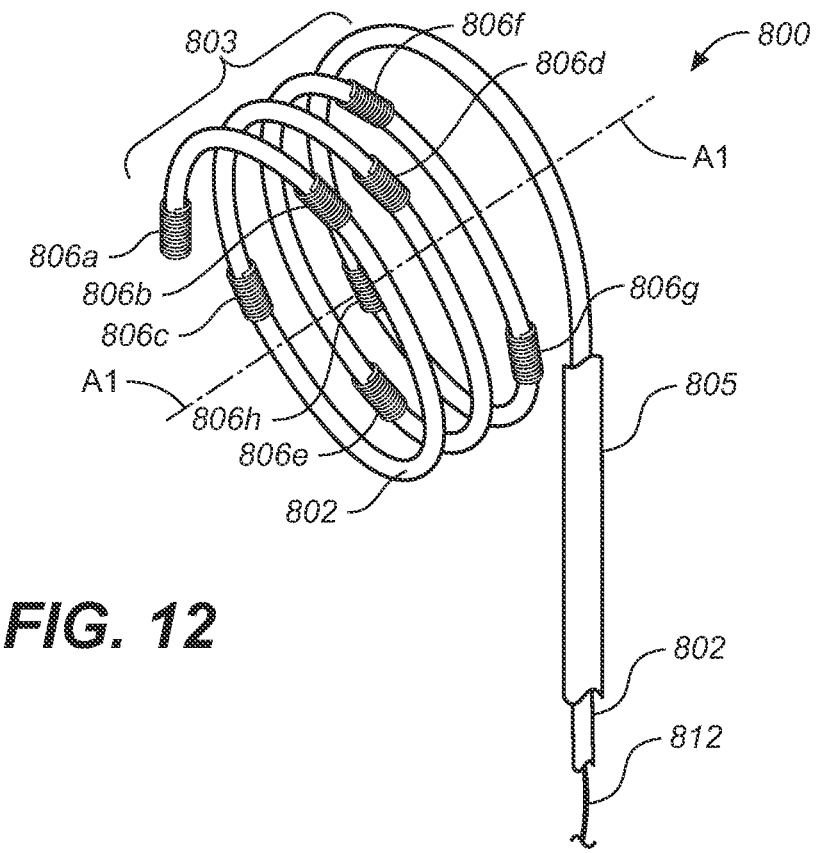
FIG. 12 illustrates another embodiment of marker sensing apparatus according to the invention.
Figure 13:
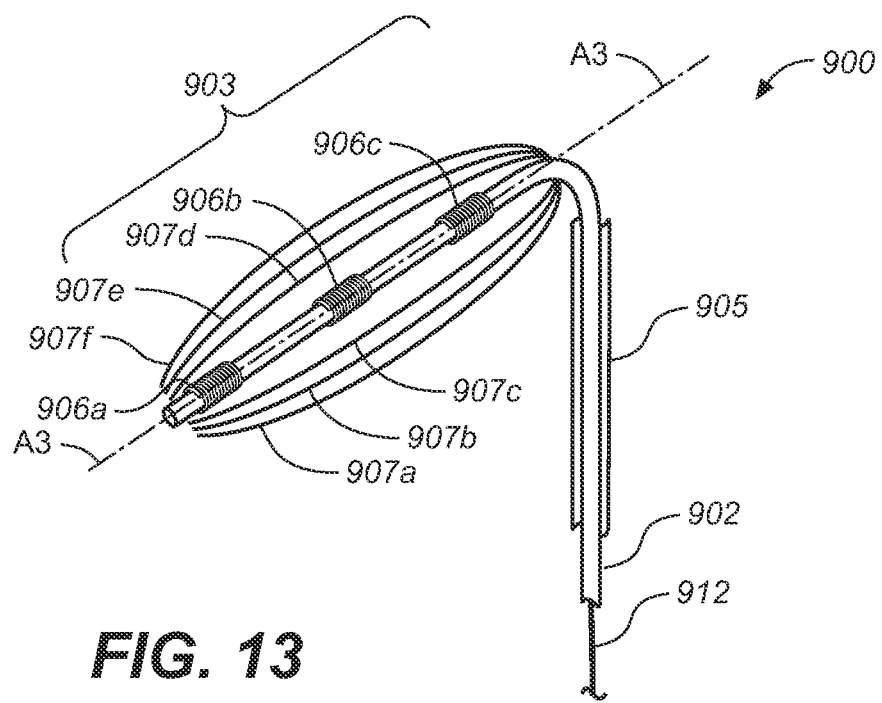
FIG. 13 illustrates a further embodiment of marker or sensing apparatus according to the invention.

Referring to FIGS. 12 and 13, further embodiments according to the invention will be described. In FIG. 12, tracked element or marker positioning apparatus is shown and generally designated with reference numeral 800. Apparatus 800 comprises an elongated member 802 having a distal end portion 803 having a memory set shape of a helical coil with periodically spaced markers, which can be in the form of sensors (e.g., EMF coils), along the length of the helix to mark a vessel (e.g., a branch vessel) inner wall surface. When the markers are EMF coils, they can be subjected to electromagnetic fields to induce electrical signal therefrom as described above. This information can be processed by measurement unit 508 and controller 506 to display a three-dimensional virtual reconstruction of the portion vessel in which the apparatus is positioned.

Elongated member 802 is slidably disposed in tubular sheath 805 which restrains distal end portion 803 in a deformed shape that generally corresponds to the shape of the sheath during delivery to the target site. When the sheath is retracted, the distal end portion returns to its memory set helical configuration. If the dimensions of the vessel do not allow it to fully return to its free state, it still tends to return to the approximate shape of its memory set configuration. The distal end portion typically will have about 2-8 tracked elements (e.g., coils) distributed therealong. In the illustrative example, eight coils 806a, 806b, 806c, 806d, 806e, 806f, 806g, and 806h are shown attached to distal portion 803. A conductor or lead extends from each tracked element or coil through a lumen in elongated member shaft 802. The leads are bundled in conductor bundle 812, which is coupled to circuit 500.

The position and orientation of tracked elements 806a-h can be mapped against preprocedural data to display vessel position and orientation as well. This can be done in a similar manner to that in described in Example 1. Prior to the surgical procedure, a detailed three-dimensional data set of the vasculature of interest (e.g., the abdominal aorta) is acquired. The patient is scanned using either a CT, CTA, MRI, or MRA scanner to generate a three-dimensional model of the vasculature to be tracked (e.g., the abdominal aorta). Tracked element or marker positioning apparatus 800 is positioned in the branch vessel (e.g., BV1) using conventional fluoroscopic techniques. A secondary imaging step is made where a two-dimensional fluoroscopic X-ray is taken to obtain a two-dimensional data set of coils 800a-h. The three-dimensional pre-procedural scan is then registered with the two-dimensional data set. This can be done using known registration techniques such as the technique described in U.S. Patent Publication No. 2004/0215071 to Frank, et al, the disclosure of which is hereby incorporated herein by reference in its entirety. This will allow real time updating (supplementation) of the pre-procedural data set for the branch vessel(s) or image thereof to display a main vessel (e.g., aorta) and branch vessel (e.g., renal artery) in real time, i.e., if you know the locations of the renals based on the measured positions of catheters inserted into the renals, then this information can be combined with an earlier scan (not necessarily acquired using a dynamic reference frame) to perform a registration of the tracker coordinate system with the image coordinate system. The alternative is to use two images as noted earlier for performing this registration. A secondary imaging step can be used for registration, but the known location of the BVs could also be used as a basis for registering the pre-operative images without the need for a secondary image.

System 800 can be used to deploy stent-grafts below or above the renal arteries. Where the AAA disease requires aortic graft sealing and fixation superior to one or both renal artery ostia, the stent-graft can be fenestrated in situ to allow renal artery perfusion using system 800 and a puncture catheter such as puncture catheter 1100 shown in FIG. 15A.

Puncture catheter 1110 includes outer tube 1111, which typically will be in the form of a steerable guide catheter, and at least two longitudinally spaced tracked elements, 1112a and 1112b, which, for example, can be EMF coils, attached to a distal end portion or segment of tube or catheter 1110 along axis A2-A2 of the catheter (e.g., the central axis of the catheter) to produce a virtual three-dimensional reconstruction of a distal end portion or segment of the puncture catheter or simply to provide a virtual image of the central axis of the distal end portion of the catheter. In the illustrative embodiment, the coils are coaxial with axis A2-A2 and the distal segment substantially rigid to enhance the correspondence between the virtual image and the actual puncture catheter.

A radio frequency (RF) delivery member or shaft 1114 is slidably disposed in steerable hollow guide tube 1111 and typically will be concentric with guide tube 1111. Shaft 1114, which can be in the form of a hollow tube, has a RF plasma electrode 1118 at its distal tip. In the illustrative example, electrode 1118 has a conical configuration and a hole along its center axis to allow guidewire 1119 to pass therethrough as shown in FIG. 15C. Insulation 1116 can be provided between shaft 1114 and RF electrode 1118. A RF conductor (not shown) is provided between RF electrode 1118 and a RF power source (not shown) as would be apparent to one of ordinary skill in the art. In use, the catheter is oriented as shown in FIG. 15C with the electrode contacting the stent-graft graft material adjacent to the target branch vessel such as a renal artery. The electrode is energized to apply RF plasma energy to the graft material of stent-graft 620 and form an opening therein through which guidewire 1119 can be deployed. The conical shape of the electrode allows the physician to advance the electrode to dilate the opening without further use of RF energy. Such electrode advancement can be performed prior to or after guidewire deployment to widen the opening when widening is desired for branch vessel stent-graft delivery. It should be understood, however, that in any of the embodiments described herein, widening of the opening with the puncture catheter is optional. When the guidewire is oriented in the desired position in the branch vessel, the puncture catheter is withdrawn so that a branch vessel stent-graft can be tracked or guided over guidewire 1119 and deployed in the branch vessel.

A further example of a suitable RF puncture catheter to which markers such as markers 1112a and 1112b can be secured is described in U.S. patent application Ser. No. 11/557,204, entitled Cutting RadioFrequency Catheter for Creating Fenestrations and which was filed on 7 Nov. 2006.

Figure 16A:
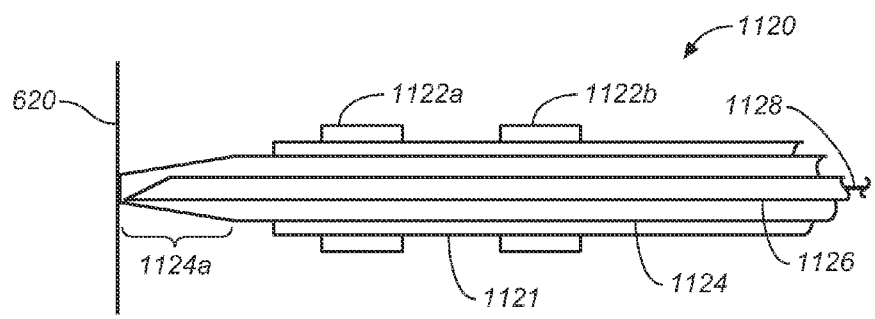
FIGS. 16A-C diagrammatically illustrate a further puncture catheter where
Figure 16B:
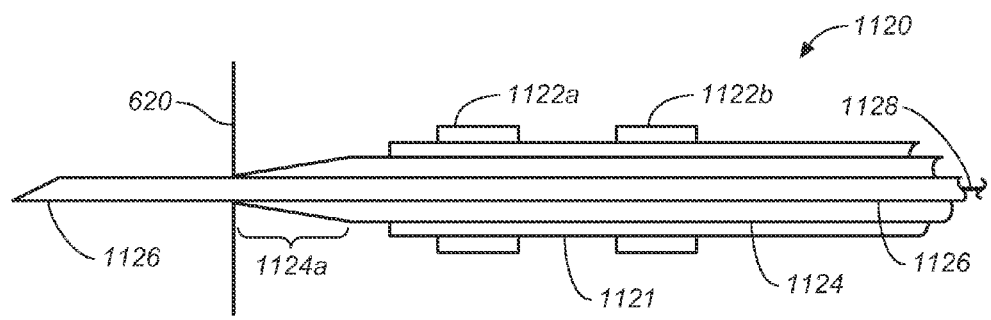
Figure 16C:
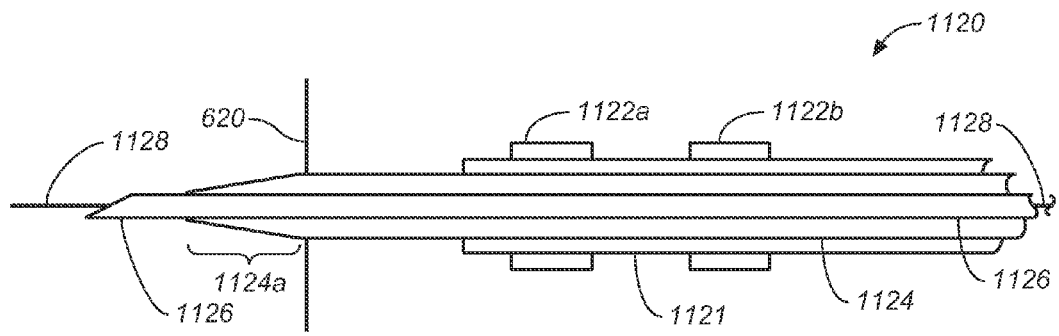

Referring to FIGS. 16A-C, another embodiment of a puncture catheter is shown and generally designated with reference numeral 1120. Puncture catheter 1120 includes outer tube 1121, which typically will be in the form of a steerable guide catheter, and at least two longitudinally spaced tracked elements, 1122a and 1122b, which, for example, can be EMF coils, attached to a distal end portion or segment of tube or catheter 1120 along an axis of the catheter (e.g., the central axis of the catheter) to produce a virtual three-dimensional reconstruction of a distal end portion of the puncture catheter or simply to provide a virtual image of an axis of the catheter (e.g., the central axis of the distal end portion of the catheter). In the illustrative embodiment, the coils are coaxial with the center axis of the distal end portion or segment of the catheter and the distal segment is substantially rigid to enhance the correspondence between the virtual image and the actual puncture catheter.

Puncture catheter 1120 further comprises inner tube 1124, which is slidably mounted in outer tube 1121, and hollow needle or piercing member 1126, which is slidably mounted in inner tube 1124. Outer tube 1121, inner tube 1124, and needle 1126 typically are concentric. Inner tube 1124 includes a tapered distal end portion 1124a, which in the illustrative example has a frustoconical shape. Distal end portion 1124a facilitates widening of the opening that needle 1126 makes. Accordingly, inner tube 1121 can be referred to as a dilator. Needle 1126 has a distal tip configured to penetrate or pierce graft material. It can have a beveled shape as shown in FIGS. 16A-C. Alternatively, it can have bullet shape, cone shape, or other suitable shape.

In use, puncture catheter 1120 is tracked to the target site in the same manner as puncture catheter 1110. The inner tube and/or outer tube can be placed in contact with stent-graft 620 as shown in FIG. 16A or they can be spaced from the stent-graft. Piercing member 1128 is then advanced through the graft material of stent-graft 620 to form a hole therein through which guidewire 1128 can be deployed. Dilator or inner tube 1124 is advanced prior to or after guidewire deployment to widen the opening with tapered portion 1124a when widening is desired for branch vessel stent-graft delivery. It should be understood, however, that in any of the embodiments described herein, widening of the opening with the puncture catheter is optional. When the guidewire is oriented in the desired position in the branch vessel, the puncture catheter is withdrawn so that a branch vessel stent-graft can be tracked or guided over guidewire 1128 and deployed in the branch vessel.

EXAMPLE 3

Figure 15A:
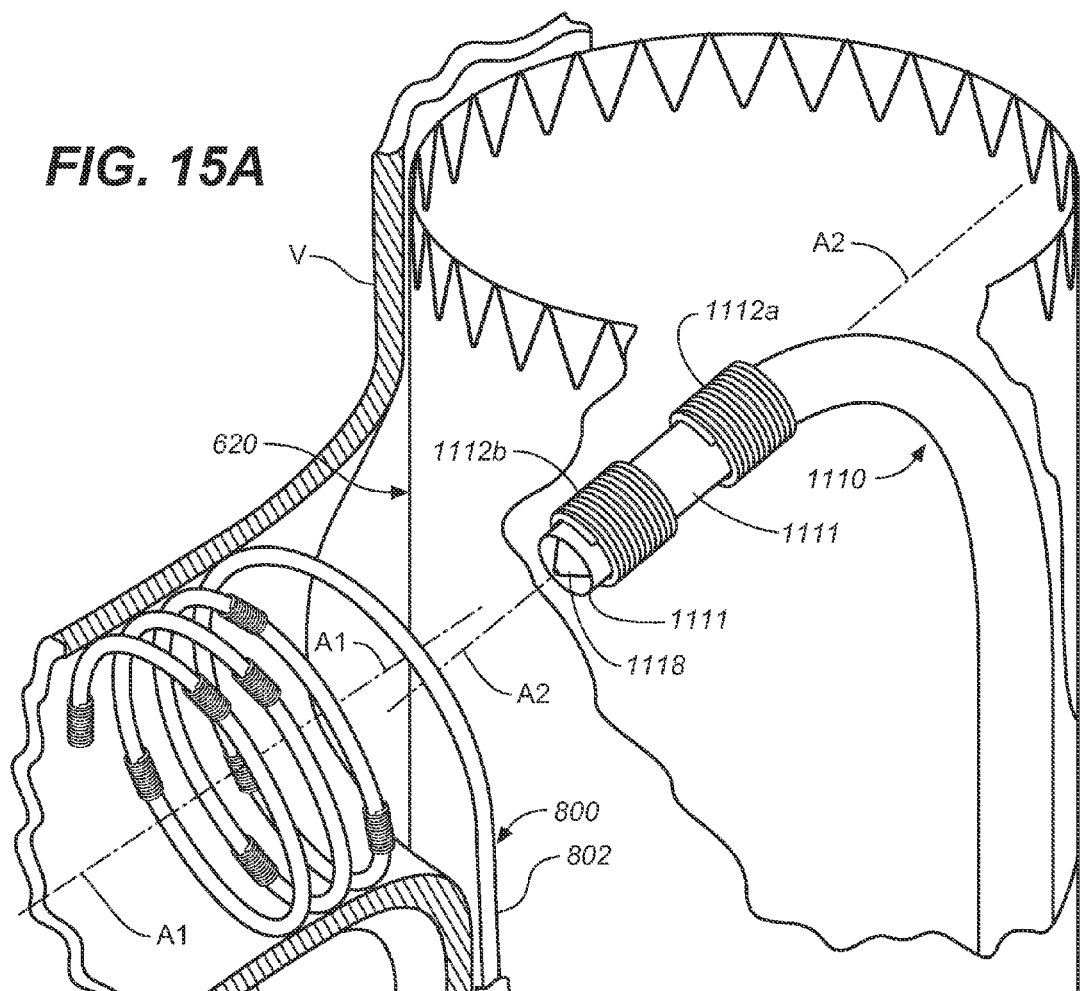
FIG. 15A illustrates use of the embodiment of FIG. 12 with a variation of the puncture device.
Figure 15B:
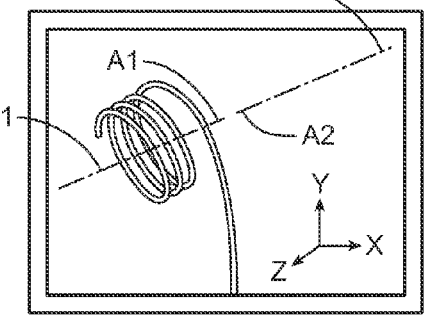
FIG. 15B illustrates an image of the apparatus of depicted in FIG. 15A.
Figure 15C:
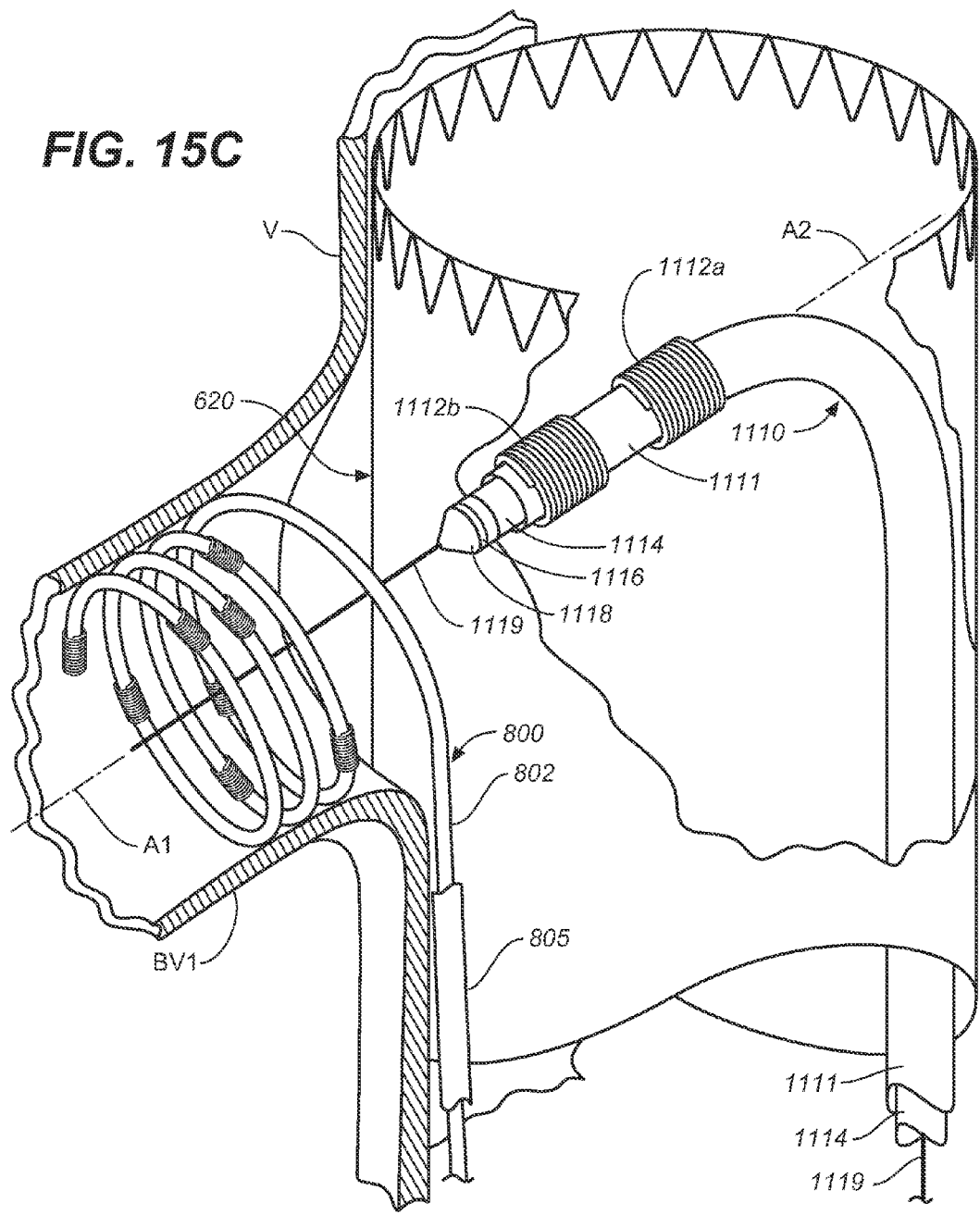
FIG. 15C illustrates the apparatus of FIG. 15A with the puncture catheter penetrated through the graft material.

Referring to FIGS. 15A-C, an exemplary operation of system 800 where electromagnetic coil type tracked elements or markers are used in conjunction with circuit 500 and puncture catheter 1110 will now be described. For the purposes of the example, the procedure involves the endovascular delivery and deployment of an AAA bifurcated stent-graft in the superior to a renal artery.

Elongated member of catheter 802 is endovascularly advanced from a femoral artery as described above into a branch vessel BV1, which in this example is a renal artery, using conventional fluoroscopic technique. Sheath 805 is withdrawn allowing the distal end 803 to move toward its memory shape helical configuration. As it moves toward its helical configuration the sensor coils are moved toward and/or urged against the inner wall of the branch artery and generally positioned in a helical array (FIG. 15A) about axis A1-A1, which generally corresponds to the center axis of that portion of the artery. Typically, all of the sensor coils will be in contact with the inner wall of the branch artery, but this is not necessarily the case. If the stent-graft is to be placed with its proximal end above both renal arteries, another apparatus 800 is positioned with its sensor coils in the second branch vessel or renal artery.

Stent-graft 620 is positioned at the desired location and deployed using conventional fluoroscopy to the position shown in FIG. 15A. Steerable puncture catheter or fenestrating device 700 is steered through the aorta and guided toward the branch vessel with the assistance of iconic representations of the activated sensors 806a-h, 1112a, and 1112b where the puncture catheter sensors 1112a and 1112b are moved toward the helical array of sensors 806a-h.

When the distal end of the puncture catheter is in the vicinity of the branch vessel ostium as indicated by the iconic representations of the sensors, the magnetic field generators of circuit 500, which have been positioned about the patient, are again sequentially activated to induce the sensors to generate voltage signals indicative of their position relative to the magnetic field generating coils as described above. This data is processed to display a real time virtual representation of center axes A1-A1 and A2-A2 in three dimensional space. The display assists the physician in orienting the puncture catheter so that axis A1-A1 is substantially or generally collinear with axis A2-A2. That is, axes A1-A1 and A2-A2 can be displayed and the puncture catheter energized so that RF plasma electrode 1118 applies RF plasma energy to the graft material of stent-graft 620 and forms a hole in the graft, while maintaining the axes aligned as shown in FIGS. 15B and 15C so that the opening is aligned or substantially collinear with those axes. Guidewire 1119 is then advanced through electrode 1118 and into branch vessel BV1 (FIG. 15C). The fenestration or opening is widened by advancing electrode 1119, which has a conical shape that mechanically widens the opening. This can be performed before or after guidewire deployment. Alternatively, the puncture catheter is withdrawn and a separate dilator system used such as system 1000 described below. A branch vessel stent-graft can be tracked over guidewire 1119 and deployed in the branch vessel as described above.

The foregoing approach addresses the challenge of identifying the circumference and the dimensional orientation of branch arteries to allow effective stent-graft fenestration in-situ, while minimizing the risk of inadvertent puncture of the aorta.

Referring to FIG. 13, another tracked element or marker positioning apparatus is shown and generally indicated with reference number 900. System 900 includes an elongated member 902 having a distal end portion 903 having central member and a plurality of members 907*a-f* circumferentially arranged therearound. The circumferentially arranged members have a radially expanded memory set configuration as shown and the central member has periodically spaced tracked elements or markers 906*a*, 906*b*, and 906*c*, which can be, for example, electromagnetic field (EMF) coils, attached thereto. The markers and central member are coaxially arranged. In this manner, the tracked elements or markers can mark an axis that generally corresponds the centerline of distal end portion 903 and/or the portion of a vessel (e.g., a branch vessel) in which the distal end portion 903 is placed. When the markers are activated, signals received therefrom can be processed to display iconic representations of the markers and a virtual image of the centerline on display 510.

Elongated member 902 is slidably disposed in tubular sheath 905, which restrains distal end portion 903 in a deformed shape that generally corresponds to the shape of the sheath during delivery to the desired vessel. When the sheath is retracted, the distal end portion returns to its memory set configuration. If the dimensions of the vessel do not allow it to fully return to its free state, it still tends to return to its memory set configuration as the members 907*a-f* are urged against the inner wall of the vessel.

Distal end portion 903 typically will have about three markers distributed therealong. A conductor or lead extends from each marker or coil through a lumen in elongated member shaft 902. The leads are bundled in conductor bundle 912, which is coupled to circuit 500. As apparent from the foregoing, system 900 can be coupled to circuit 500 manipulate puncture catheter 700' to align axes A2-A2 and A3-A3 prior to fenestration of a stent-graft positioned with its proximal end superior to one or more branch vessels such as the renal arteries.

Each distal end portion 803 and 903 can be made from be made from shape memory material and provided with a preshaped memory set configuration as shown in FIGS. 12 and 13. For example, distal portions 803 or 903 can be nitinol wire and placed in the desired shape (e.g., that shown in FIG. 12 or 13) and heated for about 5-15 minutes in a hot salt bath or sand having a temperature of about 480-515° C. It can then be air cooled or placed in an oil bath or water quenched depending on the desired properties. In one alternative, distal end portions 803 or 903 can be stainless steel and preshaped with known techniques to assume the configuration shown in FIGS. 12 and 13 when in a free or relaxed state.

Figure 14:
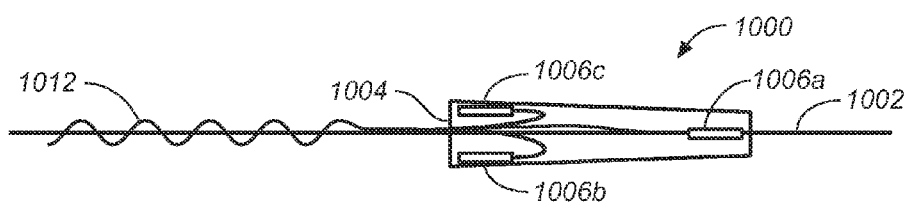
FIG. 14 depicts another embodiment of a prosthesis opening widening device with marker or sensing apparatus.

Referring to FIG. 14, another embodiment of tracked element or marker positioning apparatus is shown and generally indicated with reference numeral 1000. Apparatus 1000 includes guidewire 1002, frustoconical dilator 1004, which is coaxial with guidewire 1002 and fixedly secured thereto, tracked elements or markers 1006*a*, 1006*b*, and 1006*c*, which function in a similar manner as the markers described above and can be EMF sensing coils, for example, and lead bundle 1012, which is a bundle of three discrete conductors, each of which electrically couples a respective tracked element or marker to circuit 500. This embodiment can be used when the puncture catheter does not include a dilator and/or guidewire. The markers 1006*a,b,c* are used to track apparatus 1000 to the stent-graft wall opening in the same manner as marker 706 is used to track puncture catheter 700 to the target site.

In the example where the tracked elements or markers described herein are leadless magnetically sensitive, electrically conductive sensing coils, any suitable electromagnetic field generating and signal processing circuit or circuits for locating the position of one or a plurality of markers in three dimensions can be used.

Figure 17A:
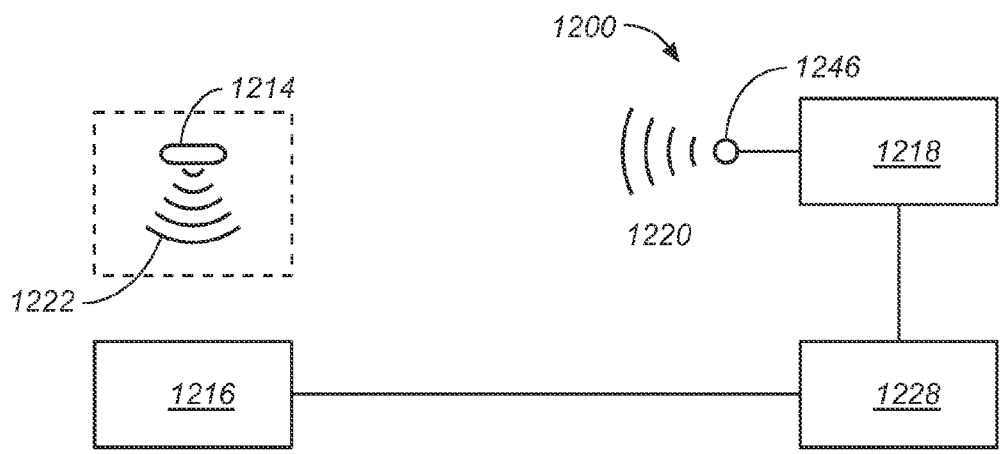
FIG. 17A diagrammatically illustrates a known system for energizing and locating leadless electromagnetic markers.
Figure 17B:
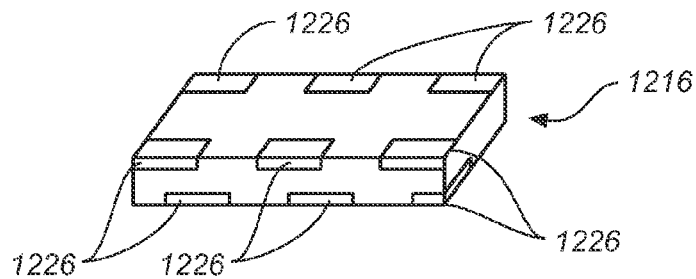
FIG. 17B is a schematic isometric view of the receiver of FIG. 17A.
Figure 17C:
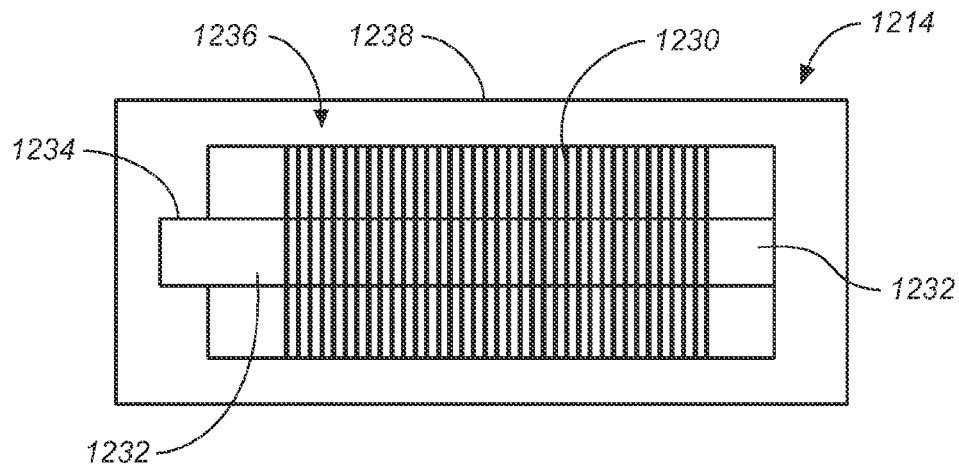
FIG. 17C is a diagrammatical section view of a known leadless electromagnetic marker.

FIGS. 17A-C illustrate an example of a leadless tracked element or marker system and components for generating an excitation signal for activating a resonating leadless tracked element or marker assembly and locating the tracked element or marker in three-dimensional space. FIG. 17A is a schematic view of a system 1200 for energizing and locating one or more leadless resonating marker assemblies 1214 in three-dimensional space relative to a sensor array 1216 where one marker assembly 1214 is shown in this example. System 1200 includes a source generator 1218 that generates a selected magnetic excitation field or excitation signal 1220 that energizes each marker assembly 1214. Each energized marker assembly 1214 generates a measurable marker signal 1222 that can be sufficiently measured in the presence of both the excitation source signal and environmental noise sources. The marker assemblies 1214 can be positioned in or on a selected object (e.g., a probe, microcatheter, or puncture catheter) in a known orientation relative to each other as described above. The marker signals 1222 are measured by a plurality of sensors 1226 in the sensor array 1216 (see FIG. 17B), which are positioned external to the patient. The sensors 1226 are coupled to a signal processor 1228 that utilizes the measurement of the marker signals 1222 from the sensors 1226 to calculate the location of each marker assembly 1214 in three-dimensional space relative to a known frame of reference, such as the sensor array 1216, for display on a display such as display 16 (FIG. 1) which also can be coupled to an imaging device as described above.

Source generator 1218 is configured to generate the excitation signal 1220 so that one or more marker assemblies 1214 are sufficiently energized to generate the marker signals 1222. The source generator 1218 can be switched off after the marker assemblies are energized. Once the source generator 1218 is switched off, the excitation signal 1220 terminates and is not measurable. Accordingly, sensors 1226 in sensor array 1216 will receive only marker signals 1222 without any interference or magnetic field distortion induced by the excitation signal 1220. Termination of the excitation signal 1220 occurs before a measurement phase in which marker signals 1222 are measured. Such termination of the excitation signal before the measurement phase when the energized marker assemblies 1214 are generating the marker signals 1222 allows for a sensor array 1216 of increased sensitivity that can provide data of a high signal-to-noise ratio to the signal processor 1228 for extremely accurate determination of the three-dimensional location of the marker assemblies 1214 relative to the sensor array or other frame of reference.

The miniature marker assemblies 1214 in the system 1200 are inert, activatable assemblies that can be excited to generate a signal at a resonant frequency measurable by the sensor array 1216 remote from the target on which they are placed. The miniature marker assemblies 1214 have, as one example, a diameter of approximately 2 mm and a length of approximately 5 mm, although other marker assemblies can have different dimensions. An example of such marker detection systems are described in detail in U.S. Patent Publication No.

20020193685 entitled Guided Radiation Therapy System, filed Jun. 8, 2001 and published on Dec. 19, 2002, and U.S. Pat. No. 6,822,570 to Dimmer et al., entitled System For Spacially Adjustable Excitation Of Leadless Miniature Marker, all of the disclosures of which are incorporated herein in their entirety by reference thereto.

Referring to FIG. 17C, the illustrated marker assembly 1214 includes a coil 1230 wound around a ferromagnetic core 1232 to form an inductor (L). The inductor (L) is connected to a capacitor 1234, so as to form a signal element 1236. Accordingly, the signal element 1236 is an inductor (L) capacitor (C) resonant circuit. The signal element 1236 can be enclosed and sealed in an encapsulation member 1238 made of plastic, glass, or other inert material. The illustrated marker assembly 1214 is a fully contained and inert unit that can be used, as an example, in medical procedures in which the marker assembly is secured on and/or implanted in a patient's body as described in U.S. Pat. No. 6,822,570 (supra).

The marker assembly 1214 is energized, and thus activated, by the magnetic excitation field or excitation signal 1220 generated by the source generator 1218 such that the marker's signal element 1236 generates the measurable marker signal 1222. The strength of the measurable marker signal 1222 is high relative to environmental background noise at the marker resonant frequency, thereby allowing the marker assembly 1214 to be precisely located in three-dimensional space relative to sensor array 1216.

The source generator 1218 can be adjustable to generate a magnetic field 1220 having a waveform that contains energy at selected frequencies that substantially match the resonant frequency of the specifically tuned marker assembly 1214. When the marker assembly 1214 is excited by the magnetic field 1220, the signal element 1236 generates the response marker signal 1222 containing frequency components centered at the marker's resonant frequency. After the marker assembly 1214 us energized for a selected time period, the source generator 618 is switched to the "off" position so the pulsed excitation signal 1220 is terminated and provided no measurable interference with the marker signal 1222 as received by the sensor array 1216.

The marker assembly 1214 is constructed to provide an appropriately strong and distinct signal by optimizing marker characteristics and by accurately tuning the marker assembly to a predetermined frequency. Accordingly, multiple uniquely tuned, energized marker assemblies 1214 may be reliably and uniquely measured by the sensor array 1216. The unique marker assemblies 1214 at unique resonant frequencies may be excited and measured simultaneously or during unique time periods. The signal from the tuned miniature marker assembly 1214 is significantly above environmental signal noise and sufficiently strong to allow the signal processor 1228 (FIG. 17A) to determine the marker assembly's identity, precise location, and orientation in three dimensional space relative to the sensor array 1216 or other selected reference frame.

A system corresponding to system 1200 is described in U.S. Pat. No. 6,822,570 to Dimmer et al., entitled System For Spacially Adjustable Excitation Of Leadless Miniature Marker and which was filed Aug. 7, 2002, the entire disclosure of which is hereby incorporated herein in its entirety by reference thereto. According to U.S. Pat. No. 6,822,570, the system can be used in many different applications in which the miniature marker's precise three-dimensional location within an accuracy of approximately 1 mm can be uniquely identified within a relatively large navigational or excitation volume, such as a volume of 12 cm×12 cm×12 cm or greater. One such application is the use of the system to accurately track the position of targets (e.g., tissue) within the human body. In this application, the leadless marker assemblies are implanted at or near the target so the marker assemblies move with the target as a unit and provide positional references of the target relative to a reference frame outside of the body. U.S. Pat. No. 6,822,570 further notes that such a system could also track relative positions of therapeutic devices (i.e., surgical tools, tissue, ablation devices, radiation delivery devices, or other medical devices) relative to the same fixed reference frame by positioning additional leadless marker assemblies on these devices at known locations or by positioning these devices relative to the reference frame. The size of the leadless markers used on therapeutic devices may be increased to allow for greater marker signal levels and a corresponding increase in navigational volume for these devices.

Other examples of leadless markers and/or devices for generating magnetic excitation fields and sensing the target signal are disclosed in U.S. Pat. No. 6,889,833 to Seiler et al. and entitled Packaged Systems For Implanting Markers In A Patient And Methods For Manufacturing And Using Such Systems, U.S. Pat. No. 6,812,842 to Dimmer and entitled Systems For Excitation Of Leadless Miniature Marker, U.S. Pat. No. 6,838,990 to Dimmer and entitled Systems For Excitation Of Leadless Miniature Marker, U.S. Pat. No. 6,977,504 to Wright et al. and entitled Receiver Used In Marker Localization Sensing System Using Coherent Detection, U.S. Pat. No. 7,026,927 to Wright et al. and entitled Receiver Used In Marker Localization Sensing System And Having Dithering In Excitation, and U.S. Pat. No. 6,363,940 to Krag and entitled System and Method For Bracketing And Removing Tissue all the disclosures of which are hereby incorporated herein in their entirety by reference thereto.

Another example of a suitable non-ionizing localization approach that accommodates wireless markers is the Calypso® 4D Localization System, which is a target localization platform based on detection of AC electromagnetic markers, called Beacon® transponders, which are implantable devices. These localization systems and markers have been developed by Calypso® Medical Technologies (Seattle, Wash.).

Any feature described in any one embodiment described herein can be combined with any other feature of any of the other embodiments whether preferred or not. For example, wireless markers can be used in any of the embodiments described herein.

Variations and modifications of the devices and methods disclosed herein will be readily apparent to persons skilled in the art.

What is claimed is:

1. A method of real time monitoring the position of a portion of a second vessel, which branches from a first vessel in a human patient comprising:
   acquiring a multi-dimensional data set of a portion of first and second vessels where the second vessel branches from the first vessel;
   delivering at least one marker attached to a catheter in vivo to one of the first and second vessels at a juncture where the second vessel branches from the first vessel;
   securing the marker to one of the first and second vessels at the juncture where the second vessel branches from the first vessel by expanding a stent-graft to pin at least the catheter to which the at least one marker is attached against a wall of the first vessel;
   determining the position of the marker in real time; and
   updating the position of a portion of the multi-dimensional data set relative to the juncture between the first and second vessels in real time based on change in position of the marker caused by motion of the anatomy of the human patient.

2. The method of claim 1 wherein acquiring the multi-dimensional data set comprises acquiring a three-dimensional data set.

3. The method of claim 2 including displaying the updated position of a portion of the three-dimensional data set in real time.

4. The method of claim 3 wherein displaying the updated position of a portion of the three-dimensional data set comprises displaying an image of the second vessel ostium in real time.

5. A method of forming an opening in a prosthesis, having a tubular wall, in vivo, comprising the steps of:
   positioning a plurality of electromagnetic coils in a second vessel that branches from a first vessel in a human patient in a configuration that has an axis that extends generally along the central axis of a portion of the second vessel;
   endovascularly positioning a tubular prosthesis in the first vessel such that it overlaps an ostium of the second vessel that opens to the first vessel
   introducing a puncture device having a distal end portion having a second axis and a proximal end portion in the prosthesis, wherein the distal end portion of the puncture device includes electromagnetic coils attached thereto that are spaced along the second axis thereof;
   generating electromagnetic fields about the plurality of coils in the second vessel and the coils attached to the puncture device distal end portion;
   processing signals from the plurality of coils in the second vessel to create a three-dimensional model of the axis of the configuration of coils and processing signals from the coils of the puncture device distal end portion to create a three-dimensional model of the second axis;
   aligning the axis of the configuration of coils that extends generally along the central axis of the portion of the second vessel and the second axis of the puncture device distal end portion such that they are substantially coaxial;
   advancing the distal end portion of the puncture device through a portion of the tubular wall of the prosthesis while maintaining the axes substantially coaxial; and
   forming an opening in the tubular prosthesis adjacent to the second vessel ostium.

6. The method of claim 5 wherein the plurality of coils are arranged in a helical array.

7. The method of claim 5 wherein the plurality of coils are oriented in a generally circular array.

8. A method of forming an opening in a prosthesis, having a tubular wall, in vivo, comprising the steps of:
   positioning a plurality of electromagnetic coils in a second vessel that branches from a first vessel in a human patient in a configuration that has a first axis that extends generally along the central axis of a portion of the second vessel;
   endovascularly positioning a tubular prosthesis in the first vessel such that it overlaps an ostium of the second vessel that opens to the first vessel;
   introducing a puncture device in the first vessel where the puncture device has a distal end portion and a proximal end portion and the distal end portion has a pair of antenna coils aligned with a longitudinal axis of the distal end portion;
   generating electromagnetic fields about the coils in the second vessel and the puncture device antenna coils;
   processing signals from the puncture device antenna coils and second vessel coils and generating a three-dimensional model of the longitudinal axis of the distal end portion of the puncture device and the first axis of the configuration of coils;
   aligning the puncture device distal end portion longitudinal axis with the first axis;
   advancing the distal end portion of the puncture device through a portion of the tubular wall of the prosthesis while maintaining the axes substantially aligned; and
   forming an opening in the tubular prosthesis adjacent to the second vessel ostium.

9. The method of claim 8 wherein the plurality of coils are arranged in a helical array.

10. The method of claim 8 wherein the plurality of coils are oriented in a generally circular array.

11. The method of claim 1 further comprising the steps of:
    acquiring a three-dimensional data set of the portion of the first and second vessels prior to acquisition of the multi-dimensional data set;
    registering the data sets; and
    associating the marker position with one of the data sets.

12. The method of claim 11 wherein acquiring the multi-dimensional data set comprises acquiring a two-dimensional data set.

13. The method of claim 11 wherein acquiring the multi-dimensional data set comprises acquiring a three-dimensional data set.

* * * * *